US007384923B2

(12) United States Patent
Gregoriadis

(10) Patent No.: US 7,384,923 B2
(45) Date of Patent: Jun. 10, 2008

(54) LIPOSOMES

(75) Inventor: Gregory Gregoriadis, London (GB)

(73) Assignee: Lipoxen Technologies Limited, London (GB)

( * ) Notice: Subject to any disclaimer, the term of this patent is extended or adjusted under 35 U.S.C. 154(b) by 135 days.

(21) Appl. No.: 10/617,734

(22) Filed: Jul. 14, 2003

(65) Prior Publication Data

US 2004/0043954 A1 Mar. 4, 2004

Related U.S. Application Data

(63) Continuation-in-part of application No. 09/254,695, filed on May 14, 1999, now abandoned.

(51) Int. Cl.
*A61K 31/70* (2006.01)
*A61K 9/127* (2006.01)
*C12P 21/06* (2006.01)
*C12N 21/00* (2006.01)

(52) U.S. Cl. .................... 514/44; 424/450; 435/320.1; 435/69.1

(58) Field of Classification Search ..................... None
See application file for complete search history.

(56) References Cited

U.S. PATENT DOCUMENTS

| | | | |
|---|---|---|---|
| 4,515,736 A | 5/1985 | Deamer | |
| 4,897,355 A | 1/1990 | Eppstein et al. | |
| 4,946,787 A | 8/1990 | Eppstein et al. | |
| 5,049,386 A | 9/1991 | Eppstein et al. | |
| 5,208,036 A | 5/1993 | Eppstein et al. | |
| 5,264,618 A * | 11/1993 | Felgner et al. | 560/224 |
| 5,366,737 A | 11/1994 | Eppstein et al. | |
| 5,459,127 A | 10/1995 | Felgner et al. | |
| 5,545,412 A | 8/1996 | Eppstein et al. | |
| 5,550,289 A | 8/1996 | Eppstein et al. | |
| 5,567,433 A * | 10/1996 | Collins | 424/450 |
| 5,593,972 A * | 1/1997 | Weiner et al. | 514/44 |
| 5,622,712 A | 4/1997 | Eppstein et al. | |
| 5,661,025 A | 8/1997 | Szoka, Jr. et al. | |
| 5,830,878 A | 11/1998 | Gorman et al. | |

FOREIGN PATENT DOCUMENTS

| | | |
|---|---|---|
| EP | 0187702 A1 | 7/1986 |
| EP | 0172007 B1 | 5/1991 |
| EP | 0475178 | 3/1992 |
| JP | 1-047381 | 2/1989 |
| JP | 2-135092 | 5/1990 |
| WO | 90/11092 | 10/1990 |
| WO | WO 91/17424 | 11/1991 |
| WO | 93/14778 | 8/1993 |
| WO | WO 95/04524 | 2/1995 |
| WO | WO 95/13796 | 5/1995 |
| WO | WO 95/24485 * | 9/1995 |

OTHER PUBLICATIONS

Barouch et al (Intervirology 2000 43: 282-287).*
Bende et al (AIDS Read. 10(9): 526-528,530-532,534-538, (Sep. 2000).*
Peters (Vaccine 20: 688-705, 2002).*
Abrignani (J. Hepatol. 31 (Suppl. 1): 259-263, 1999).*
Koff (Int. J. Parisitol. 33: 517-523, 2003).*
Prince (FEMS Microbiol. Rev. 14(3): 273-277, 1994).*
Hunziker et al (Mol. Immunol. 38: 475-484, 2001).*
Kirby et al (Bio/Technology (1984), 2(11), 979 84).*
P.L. Felgner, et al., "Nomenclature for Synthetic Gene Delivery Systems", Human Gene Therapy, 8:511-512, Mar. 20, 1997.
Christopher Kirby, et al., "Dehydration-Rehydration Vesicles: A SimpleMethod for High Yield Drug Entrapment in Liposomes", Research Paper: Academic Department of Medicine, Royal Free Hospital School of Medicine, University of London, Biotechnology, Nov. 1984, pp. 979-984, Bio/Technology 2(11) 979-984.
Y. Perrie, et al., "Liposome Entrapped Plasmid DNA: Characterisation Studies" Biochim. Biophys. Acta 1475 (2000) , pp. 125-132.
G. Gregoriadis, et al., "Liposomes Mediated DNA Vaccination", FEBS Letters 402 (1997), pp. 107-110.
A. Bacon, et al., "Induction of a Cytotoxic T Lymphocyte (CTL) Response to Plasmid DNA Delivered Via Lipodine Liposomes," Journal of Liposome Research, 12 (1&2), (2002), pp. 173-183.
Y. Perrie, et al., "Liposome Mediated DNA Vaccination: The effect of vesicle composition" Vaccine 19 (2001), pp. 3301-3310.
G. Gregoriadis, "Drug and Vaccine Delivery Systems," In: PharmaTech 2001, World Markets Research Centre Ltd., (2001), pp. 172-176.
G. Gregoriadis, "Genetic Vaccines: Strategies for Optimization", Pharmaceutical Research vol. 15, No. 5 (1998), pp. 661-670.
"Genetic Chemistry: Towards non-enzymatic . . . " in Targeting of Drugs: Strategies for Oligonucleotide and Gene Delivery in Therapy, eds Gregoriadis, G. and McCormack, B.; Behr, J-P.; 1996, pp. 1-6.
"Immune Responses with Direct Gene Transfer: DNA Vaccines and Implications for Gene Therapy" from "Targeting of drugs . . . " op cit; Davis, HL; 1996, pp. 1-9.
High Yield Incorporation of Plasmid DNA without Liposomes: Effect on DNA Integrity and Transfection Efficiency; J. Drug Targeting (1996); 3, 469-475; Gregoriadis, G., et al.; 1995.
IBC's second annual genetic vaccines and Immunotherapeutic Strategies conference, 1996-abstract by Felgner, et al. "Synthetic Gene Delivery Systems for Nucleic Acid -Immunisation" and Ledley, FD "Gene Expression and Delivery Systems for Nucleic Acid Vaccines"; 1996.
"Enhanced Gene Delivery and Mechanism Studies with a Novel Series of Cationic Lipid Formulations"; J. Biol. Chem. (1994) 269(4) 2550-2561; Felgner, J.H., et al.; 1994.
"Synthetic Gene-Transfer Vectors", Acc. Chem. Res. (1993) 26, 274-278; Beh., J-P; 1993.

(Continued)

Primary Examiner—Richard Schnizer
(74) Attorney, Agent, or Firm—Morrison & Foerster LLP

(57) ABSTRACT

Cationic liposomes with entrapped polynucleotide in the intravesicular space are described. The liposomes include cationic components such as cationic lipids such as DOTAP. Preferably the method of forming liposomes uses the dehydration-rehydration method in the presence of the polynucleotide. The polynucleotide preferably operatively encodes an antigen capable of eliciting a desired immune response, that is, is a gene vaccine.

11 Claims, 10 Drawing Sheets

OTHER PUBLICATIONS

"Gene Transfer with Synthetic Cationic Amphiphiles; Prospects for Gene Therapy"; Bioconjugate Chemistry (1994) 5, 382-389; Behr, J-P; 1994.

"Mode of Formation and Structural Features of DNA-Cationic Liposome Complexes Used for Transfection"; Biochemistry (1993) 32,7143-7151; Gershon, et al.; 1993.

"DNA-Lipid Complexes: Stability of Honeycomb-Like and Spaghetti-like Structure" Biophysical Journal (Nov. 1997) 73, 2427-2440; May S.; Nov. 1997.

"The Structure of DNA-Liposome Complexes"; J. Am. Chem. Soc. (1997); 119, 832-833; Lasic, D.D., et al.; 1997.

"New Structures in Complex Formation Between DNA and Cationic Liposomes Visualised by Freeze-Fraction Electron Microscopy"; FEBS Letts. (1994) 356,361-366; Sternberg, B., et al.; 1994.

"Cationic Liposome-Mediated Transfection"; Nature (Jan. 1989); 337, 387-388; Felgner, P.L., et al.; Jan. 1989.

"Virus-Sized Self-Assembling Lamellar Complexes Between Plasmid DNA and Cationic Micelles Promote Gene Transfer"; Proc. Natl. Acad. Sci. USA (Dec. 1997); 94, 14412-14417; Pitard, B., et al.

"Structure of DNA Cationic Liposome Complexes: DNA Intercalation in Multilamellar Membranes in Distance Interhelical Packing Regimes"; Science (Feb. 1997); 272, 810-814; Radler, O., et al.

"Multilamellar Structures of DNA Complexes with Cationic Liposomes"; Biophysical Journal (Oct. 1997); 73, 1842-1846; Dan, N.

"Formation of Ordered Domains in Membrane-Bound DNA"; Biophysical Journal (Sep. 1996); 71, 1267-1272; Dan, N.

* cited by examiner

LIPOSOMES

This is a continuation-in-part of application Ser. No. 09/254,695, filed May 14, 1999 now abandoned, the disclosure of which is hereby incorporated by reference.

The present invention relates to compositions of liposomes with entrapped polynucleotide encoding a desired polypeptide. The polypeptide preferably encodes an immunogenic polypeptide useful to induce a desired immune response in a subject, for instance for prophylactic immunisation against infective microbes or for immunotherapeutic treatment. The liposomes preferably include at least one cationically charged lipid and are preferably made by a dehydration-rehydration technique.

It is known to introduce genetic material into the body of a human or animal subject for various purposes. In the mid 1960s it was suggested the technique could be used for the treatment of genetic diseases by introduction of a normal gene sequence into cells of a person carrying its defective counterpart. Trials are currently underway of methods of treating various inherited genetic disorders by gene therapy. For instance, a considerable amount of work has been carried out on the treatment of cystic fibrosis, by introducing DNA encoding the CF transmembrane conductance regulator. Since the gene product is required in the lungs, attempts have been made to deliver the gene directly into the lungs or intranasally.

More recently gene therapy has been proposed for treatment of cancer. For instance, by introducing genes encoding tumour necrosis factor (TNF) or interleukin-2 into lymphocytes or into tumour cells, it is hoped to stimulate an immune response resulting in tumour destruction. In addition, by introducing genes encoding a human class 1 major histocompatibility antigen (HLA-B7) into tumour cells of patients who do not express this antigen, it is hoped to stimulate an immune response to the antigen resulting in destruction of tumour cells.

A variety of vectors have been proposed for the delivery and expression of nucleic acids in gene therapy (Mulligan, 1993). They include viruses (eg. retroviruses and adenoviruses) as well as non-viral vectors (eg. cationic polymers and vesicles). However, there are disadvantages with each of these vectors, for instance possible side effects upon integration of retroviruses into the cell genome, promotion of immune responses against viral proteins thus precluding long term treatment (Kay et al, 1994), and transient or low efficiency transfection by non-viral vectors (Legendre and Szoka, 1995). Nonetheless, the relative simplicity of DNA incorporation into non-viral vectors, often regardless of DNA size and structure, and their non-pathogenic nature, render these vectors an attractive alternative. Indeed, constructs (complexes of preformed cationic vesicles and plasmid DNA) have been now developed which exhibit high indexes of transfection in vitro (Felgner, 1991) and a low to modest transfection in experimental animals (Alton et al, 1993;Zhu et al, 1993). On the other hand, because of the potential toxicity (Raz et al, 1994) of such complexes and inability to incorporate other agents which may promote DNA transfer efficiency, their usefulness in vivo may not be as promising as when nucleic acids are incorporated within conventional liposomes. These, when appropriately designed (in terms of vesicle size, surface charge and lipid composition), remain stable in the blood circulation (Scherphof et al, 1983; Gregoriadis, 1995) thus protecting their nucleic acid contents from nucleases in blood plasma, or attain clearance rates conducive to optimal use (Gregoriadis, 1995). Moreover, grafting of cell-specific ligands to the surface of long circulating liposomes would direct nucleic acids preferentially to target cells (Gregoriadis, 1995). Incorporation of other agents into nucleic acid-containing liposomes may also render them fusogenic, facilitate escape of their contents from the endosomes into the cytoplasm or promote DNA transport into the nucleus (Legendre and Szoka, 1995). However, most techniques (Gregoriadis, 1993) for the entrapment of DNA into liposomes are inefficient, incompatible with its size or employ conditions (eg. sonication, organic detergents and solvents) which may be detrimental to DNA integrity.

WO-A-9117424 (Vical, Inc) describes various complexes of positively and negatively charged lipid species and an active compound with improved intracellular delivery. It is suggested that low rates of entrapment of polynucleotide into cationic liposomes can be overcome by a method in which a net positively charged complex of preformed positively charged liposomes and polynucleotides (which are negatively charged) is subsequently associated with an excess of preformed negatively charged liposomes which are said to coat the positively charged complex. However, since the polynucleotide is not entrapped inside any vesicle, it is believed that it will be accessible to nucleases in plasma.

In U.S. Pat. No. 4,897,355 Eppstein et al (Syntex) describe liposomes formed of cationic lipid for use in intracellular delivery of active compounds. One example of active compound is a polynucleotide, for instance encoding enzymes for use in enzyme deficiency conditions, hormones for use in hormone replacement therapy, blood coagulation factors, neuro transmitters, anti-viral compounds and anti-cancer compounds or for delivery of anti-sense RNA for selectively turning off expression of certain proteins. The active compounds are admixed with preformed, empty liposomes and optionally the conjugate is subsequently admixed with further preformed liposomes.

In Journal of Drug Targeting, 1996, (in press) Gregoriadis et al described formation of liposomes with entrapped DNA for use in gene therapy made using a dehydration-rehydration technique.

At the 1995 conference "Targeting of Drugs: Strategies for Oligonucleotide and Gene Delivery in Therapy" and in the subsequent proceedings of that conference, eds. G. Gregoriadis and B McCormack (published 1996, Plenum Press, New York) Davis discusses undesirable immune response against products of genes introduced into cells for gene therapeutic processes. She suggests how the study of the immune response induced upon intracellular introduction of genes is important to optimize gene therapeutic treatments as well as DNA-vaccination (DNA-based immunisation) applications of gene transfer. She describes many advantages of gene vaccines over antigen-based vaccines and describes some results on the use of naked DNA for DNA based immunisation to Hepatitis B surface antigen (HBsAg).

At the same conference, Behr described synthetic carriers for polynucleotide sequences for gene therapy consisting of lipopolyamines which are alleged to self-assemble around DNA while condensing it. The polynucleotide is intended to reach the cell nucleus. The self-assembled particles are believed by the present inventor not to be constituted by a bilayer, and thus would not be defined as liposomes.

The pre-conference information relating to IPC's second annual conference "Genetic Vaccines and Immunotherapeutic Strategies", which took place on Oct. 23 and 24, 1996 in Washington D.C., USA, indicated Felgner would describe recent work using cationic lipid to improve delivery of genes coding for antigens. The genes are delivered intranasally and into lung tissue to stimulate mucosal immunity. At the same conference, it was asserted that Ledley would describe gene delivery systems comprising cationic lipids to control the bioavailability and entry of DNA into mucosal cells. The intention is to engineer an effective immune response. The pre-conference announcement gives no more information about how the gene delivery has been carried out.

It would be desirable to increase the encapsulation rate of polynucleotides in liposomal delivery systems. Furthermore it would be desirable to increase the level of gene product in the circulation of animals to whom the genes had been administered, especially for therapeutic products. It is, furthermore, desirable to increase the rate of delivery of the gene to target cells, where the gene product is an antigen. It would furthermore be desirable to provide improved delivery of polynucleotides encoding immunogenic polypeptides which are useful to induce a desired immune response.

A first aspect of the present invention provides a new method of generating an immune response to a target polypeptide in an animal in which an aqueous liposomal composition is administered subcutaneously or intramuscularly to the animal, the composition comprising liposomes suspended in an aqueous liquid having diameters in the range 100 to 2000 nm and comprising a lipid bilayer and an aqueous intravesicular space, the lipid bilayer being formed of liposome forming components including at least one cationically charged component in an amount such that the liposome forming components have an overall cationic charge, and the aqueous intravesicular space comprising polynucleotide operatively encoding said target polypeptide, whereby the said polynucleotide is delivered to and is expressed in target cells, to form target polypeptide and an immune response to the target polypeptide follows.

In this specification the term entrapped refers to the fact that the polynucleotide is the intravesicular space. Thus the liposomes have been formed in the presence of the polynucleotide. This is to be contrasted to the prior art complexes of preformed liposomes and polynucleotides.

The polypeptide product of the gene should be an antigen against which an immune response is desired. The polypeptide thus includes one or more antigenic determinants of infectious microorganisms, such as viruses, bacteria or fungi. The method is of particular utility in immunisation against bacteria, fungi and viruses, especially influenza, HIV, hepatitis B and hepatitis C. The gene product may therefore be hepatitis surface antigen, (HBsAg) hepatitis C core protein, an influenza antigen or an antigenic HIV peptide or fragment. The invention is also of value where the gene product is one or more herpes simplex virus proteins, a cancer virus product, such as SV40, a cancer antigen, a tuberculosis antigen, or an antigen of a more complex microorganism, such as a parasite, for instance malaria.

In this invention the target cells for liposome uptake are generally antigen presenting cells. The composition may be administered intramuscularly or subcutaneously. Such routes are preferred over, for instance, intravenous intraperitoneal routes for a variety of reasons, safety, convenience and comfort for the recipient. The present invention has allowed for the first time, successful generation of an immune response where the liposomes are administered subcutaneously. It is a preferred aspect of this invention, therefore that the composition is administered subcutaneously.

In the present specification the term "liposome" refers to vesicles surrounded by a bilayer formed of components usually including lipids optionally in combination with non-lipidic components.

It may be desirable to provide the external surface of the liposome with a targeting moiety, for instance an antibody, suitable for recognising target tissue. For instance where the composition is administered into the circulation, cell specific ligands attached to the external surface of the liposome would direct the nucleic acids to the target cells (Gregoriadis, 1995).

The gene should be present in a form such that the desired product can be produced in the target cell, and thus preferably includes regulatory elements that facilitate expression in the target cells. The polynucleotide thus includes a promoter, as well as regions to mediate ribosome binding, and optionally also other regions which might enhance gene expression.

The polynucleotide may be RNA, but is preferably DNA. It is generally in the form of a plasmid, preferably a substantially non-replicating plasmid, since for this aspect of the invention, transient activity over a period of weeks or a few months is generally appropriate.

The liposome forming components used to form the liposomes may include neutral, zwitterionic, anionic and/or cationic lipid moieties. These are used in relative amounts such as to confer an overall cationic charge on the liposome. It is found that using lipid components such that the liposome has an overall positive charge provides improved results compared to liposomes with a negative or no overall charge, in terms of giving an increase immune response when used to deliver an antigen-encoding gene. In addition to components which are properly termed lipids (including glycerides and cholesterol), the liposome forming components may include non-lipidic components (i.e. which are not naturally occurring lipids) such as non-ionic or cationic surface active agents.

It is believed that this is the first time that polynucleotide has been entrapped into a cationic liposome. Accordingly, in a second aspect of this invention there are provided liposomes formed from liposome forming components including at least one cationically charged component and polynucleotide encoding a desired polypeptide product and is characterised in that the polynucleotide is entrapped within the liposome.

Thus the present inventor has established that in an in vitro system, the entrapment of DNA encoding for luciferase marker protein gives increased levels of luciferase expression as compared to other methods using uncharged liposomes or anionically charged liposomes. Whilst the levels of expression were lower than using a complex of preformed cationically charged liposomes (the commercially available LipofectAMINE (trade mark)), it is expected that an improvement in resistance to nuclease attack by the entrapment as compared to the complex would be exhibited in vivo. In addition it is found that the liposomes do not aggregate rapidly, whereas such aggregation can occur for mixed preformed liposomes—polynucleotide systems especially in the presence of serum proteins. The entrapment of polynucleotide provides greater freedom to provide targeting ligands on the liposome surface or carrying out other surface treatments on the liposomes with entrapped actives. It is expected that the high level of expression of the model protein luciferase would be exhibited where the gene product was an antigen inducing a desired immune response.

This has been confirmed by experiments which have shown that vaccination of mice with liposome-entrapped pRc/CMV HBS (encoding the S region of hepatitis B surface antigen; subtype ayw) by a variety of routes results in humoral and cell-mediated immune responses that are independent of whether or not mice are inbred (Balb/c) or outbred (T/o) and route of injection (intramuscular, im; subcutaneous, sc; intravenous, iv; and intraperitoneal, ip). Such responses are in most cases significantly greater than those seen with naked DNA under identical conditions (see example 5 below).

In this embodiment of the invention the cationic component incorporated into the liposome may be any of those which have been used in liposome preparations for improving transfection rate by complexation with polynucleotides. The component may be a lipidic or a non lipidic compound and may be synthetic or natural. Preferred cationic lipids are, 1,2-bis(oleoyloxy)-3-(trimethylammonio)propane (DOTAP), 1,2-bis(hexadecyloxy)-3-trimethylaminopropane (BisHOP), N-[1-(2,3-dioleyloxy)propyl]-N,N,N-triethylammoniumchloride (DOTMA) and other lipids of structure I defined in U.S. Pat. No. 4,897,355, incorporated herein by reference or the ester analogues. The structure is as follows:

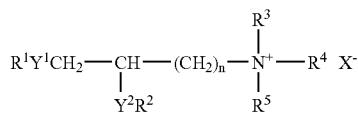

or an optical isomer thereof, wherein $Y^1$ and $Y^2$ are the same or different and are each —O— or O—C(O)— wherein the carbonyl carbon is joined to $R^1$ of $R^2$ as the case may be; $R^1$ and $R^2$ are independently an alkyl, alkenyl, or alkynyl group of 6 to 24 carbon atoms, $R^3$, $R^4$ and $R^5$ are independently hydrogen, alkyl of 1 to 8 carbon atoms, aryl or aralkyl of 6 to 11 carbon atoms; alternatively two or three of $R^3$, $R^4$ and $R^5$ are combined with the positively charged nitrogen atom to form a cyclic structure having from 5 to 8 atoms, where, in addition to the positively charged nitrogen atom, the atoms in the structure are carbon atoms and can include one oxygen, nitrogen or sulfur atom; n is 1 to 8; and X is an anion.

Preferred embodiments are compositions wherein $R^1$ and $R^2$ individually have from 0 to 6 sites of unsaturation, and have the structure

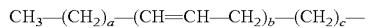

wherein the sum of a and c is from 1 to 23; and b is 0 to 6. Most preferably each of $R^1$ and $R^2$ is oleyl. Particularly preferred embodiments are compositions wherein the long chain akyl groups are fatty acids, that is, wherein $Y^1$ and $Y^2$ are alike and are —O—C(O)—.

Alternatively cationic lipids of the general structure I or the general structure II defined in U.S. Pat. No. 5,459,127, incorporated herein by reference may be used.

Other suitable cationic compounds are the non-lipid component stearylamine and 3β[N—(N'N'-dimethylaminoethane)-carbamyl]cholesterol (DC-Chol) (a lipidic component).

The liposomes, in addition to comprising cationic components, generally also comprise non-ionic and/or zwitterionic components which include lipids, which may be phospholipids or other lipids not including phosphoryl groups. Preferably the lipids include phospholipids, such as natural or synthetic phosphatidylcholines, phosphatidylethanolamines, phosphatidylserines in any of which the long chain alkyl groups (which may be joined through ester or ether linkages) may be saturated or unsaturated. Preferably the acyl groups of glyceride lipids are unsaturated. The components may include non-lipidic components, for instance non-ionic surfactants such as sorbitan mono esters of fatty acids, and/or ethoxylated fatty acids or other analogues, such as ethoxylated lanolins.

Best results are achieved when the liposomes include fusogenic lipids, which are usually phosphatidyl ethanolamines in which the acyl groups are unsaturated. Cholesterol may be included although it seems to render the liposomes too stable for adequate delivery of polynucleotide into target cells.

The amount of cationic component is preferably in the range 5 to 50% of the total moles of liposome forming components, preferably in the range 10 to 25% mole.

The liposome composition is generally in the form of an aqueous suspension for instance, a physiological buffer. Alternatively it could be a dried composition for rehydration.

The liposomes may be made by any of the generally used liposome forming techniques. The product liposomes may be multilamellar or unilamellar vesicles and may be relatively large (vesicle diameters in the range 300 nm to 2000 nm preferably with average diameters in the range 500-1000 nm), or small (vesicle diameters in the range 100 nm to 400 nm preferably with average diameters in the range 200 to 300 nm). Preferably the liposomes have a mean diameter not exceeding 500 nm, and preferably substantially all have diameters less than 2000 nm.

Preferably the liposomes are formed by a process in which the vesicles are formed, mixed with nucleotide to be entrapped and are then dehydrated, preferably by freeze drying, and subsequently rehydrated in aqueous composition to make dehydration-rehydration vesicles, and preferably subsequently subjected to micro fluidization to reduce the average size. Preferably the non-entrapped material is separated from liposomes by centrifugation or molecular sieve chromatography, after the rehydration and/or microfluidization steps.

The present inventor has established that the use of DRV's can provide increased entrapment levels for polynucleotides. According to the present invention there is provided a process for forming an aqueous suspension of liposomes having diameters in the range 100 to 2000 nm comprising the steps:

a) providing an aqueous suspension of small unilamellar vesicles forming components selected from the group consisting of lipids, cholesterol and non-ionic and cationic surface active agents including at least one cationically charged component selected from cationic lipids and cationic surface active agents present in an amount whereby the small unilamellar vesicles have an overall cationic charge;

b) adding to the aqueous suspension of small unilamellar vesicles a polynucleotide operatively encoding an immunogenic polypeptide useful to induce an immune response in an animal to form a mixed suspension;

c) dehydrating the mixed suspension to form a dehydrated mixture;

d) rehydrating the dehydrated mixture to form an aqueous suspension of dehydration-rehydration vesicles containing said nucleic acid in the intravesicular space thereof; and e) optionally subjecting the aqueous suspension of dehydration-rehydration vesicles to a further step of microfluidisation whereby the said aqueous suspension of liposomes is produced.

Dehydration is preferably by freeze-drying (lyophilisation). The dehydration-rehydration of both method aspects of the invention is substantially as described by Kirby and Gregoriadis, 1984, the content of which is incorporated herein by reference. Thus, the liposomes in step (a) are small unilamellar vesicles having diameters in the range 100 to 400 μm (SUV's) and made in step (d) are preferably multilamellar liposomes (MLV's) respectively. The product liposomes of step (d) are called dehydration-rehydration vesicles (DRV's). Micro-fluidization of the DRV's is carried out substantially as described in WO-A-92/04009, the disclosure of which is incorporated herein by reference and by Gregoriadis et al, 1990.

By using the dehydration-rehydration technique, the present inventor has established that an overall solute entrapment yield of above 10% can be achieved. The inventor has established that up to 90% or even more of the polynucleotide present in the aqueous suspension subjected to the freeze drying step can be entrapped into the liposomes. Furthermore micro-fluidization, whilst resulting in a reduction of the percentage of polynucleotide incorporated, nevertheless allows entrapment rates for polynucleotide of more than 10%, for instance up to 50%, to be achieved. The level of polynucleotide entrapment in the liposomal composition is preferably in the range 0.05 to 5, preferably 0.1 to 1.0, more preferably 0.2 to 0.5 μg/μmole lipid (or in the range 0.1 to 10 μg DNA per mg lipid).

This aspect of the invention is preferably used to make the liposomal preparations used in the method of the invention.

The invention includes also the use of the liposomes made by the novel processes of the invention in the manufacture of a composition for use in a method of therapy or prophylaxis. For instance the method may be the immunisation (vaccination) of a human or animal subject to protect it against infection by infectious microorganisms. Alternatively an immune response may be generated by the gene product which is useful in immune therapy, for instance to treat cancer.

Conventional pharmaceutical carriers used for liposomal administration can be used. The inventor has found that the invention allows injection of the cDNA using simple i.m. techniques. Where naked DNA has been used as a vaccine in the past it has been found that special highly controlled injection protocols have to be followed to avoid any damage to the muscle and to inject in exactly the same position to be able to provide reliable comparable results. For instance, it has been found that muscle regenerating agents must be preadministered to improve response. The present invention avoids such complex protocols.

The present invention is illustrated in the following examples. In some of the examples DNA encoding luciferase is used as a model polynucleotide, luciferase being a model gene product.

The drawings represent the results of some of the examples as follows.

Figure 9:
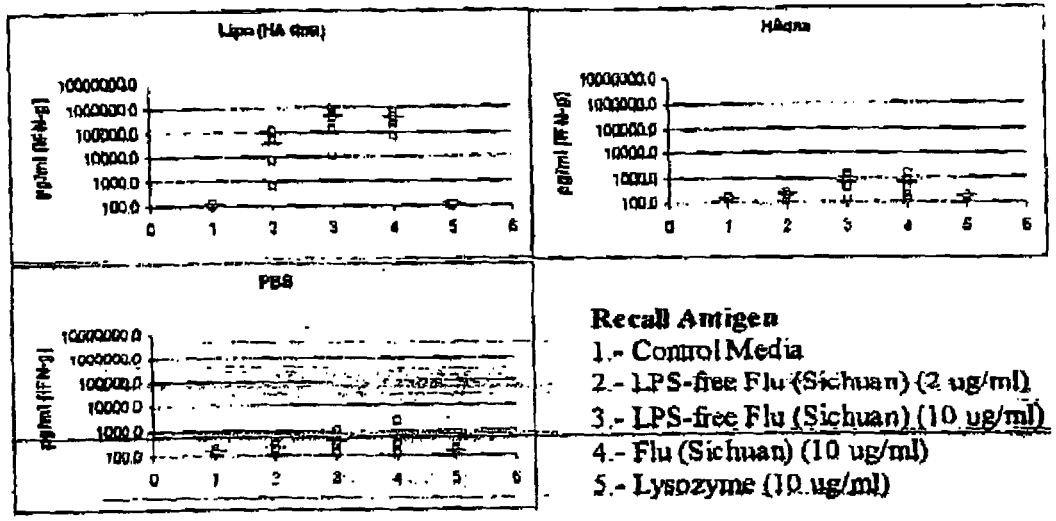

FIGS. 9a-c show the results of example 9;

FIGS. 10 to 16 show the results of example 10;

FIGS. 17 to 20 show the results of example 11; and

Figure 21:
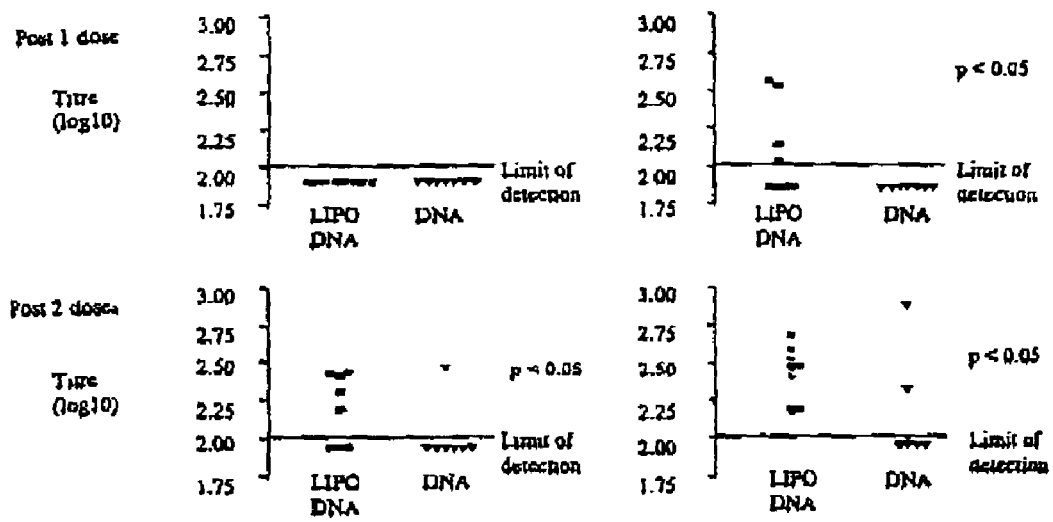
Figure 22:
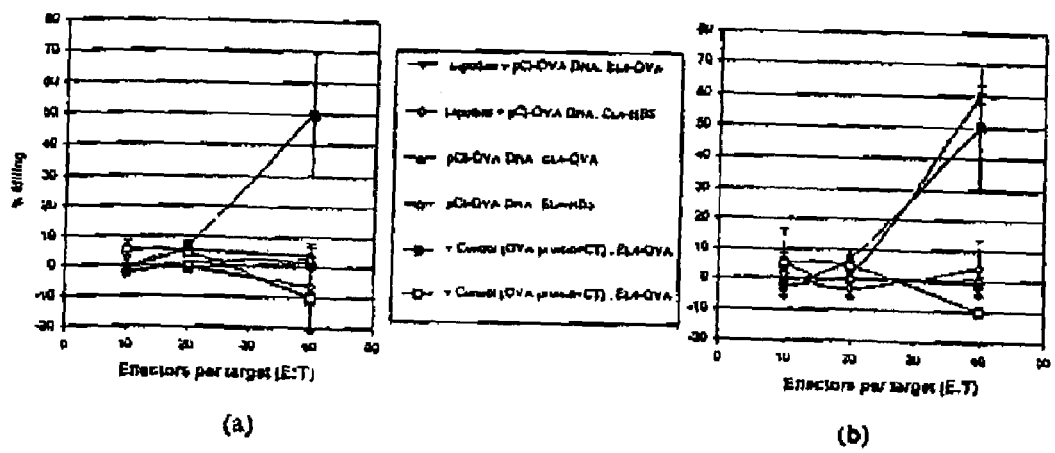

FIGS. 21 to 22 show the results of example 12.

EXAMPLE 1

Entrapment and Complexation of Luciferase Encoding DNA and In Vitro Transfection of Cells Materials The sources and grades of egg phosphatidylcholine (PC), stearylamine (SA) and 1,2-bis(hexadecyloxy)-3-trimethylaminopropane (BisHOP) have been described elsewhere (Tan and Gregoriadis, 1989). N[1-(2,3-dioleyloxy)propyl]-N,N,N-trimethylammonium (DOTMA) was a gift from GeneMedicine (Houston, Tex., USA). Phosphatidylserine (PS) and dioleoyl phosphatidylethanolamine (DOPE) were from Sigma Chemical Co. (Poole, Dorset, UK). The eukaryotic expression vector pGL2-control ($\approx 3.99 \times 10^6$ Daltons) expressing the luciferase reporter gene from a SV40 promoter was purchased from Promega (Southampton, UK). The cationic LipofectAMINE, obtained from Gibco BRL (Paisly, UK), was complexed with pGL2 in OptiMEM 1 reduced serum medium containing GLUTAMAX 1 (Gibco BRL) at a ratio of 15:1 (wt:st) before use. Deoxyribonuclease I (bovine pancreas, type II; specific activity:2500 Kunitz units $mg^{-1}$ protein) was from Sigma Chemical Co. RQ1 deoxyribonuclease (1 unit $\mu l^{-1}$) and the luciferase assay system kit were purchased from Promega. The pGL2 plasmid DNA was radiolabelled with $^{35}$S-dATP (37 kBq; ICN Flow, Thame, UK) by the method of Wheeler and Coutelle (1995). All other reagents were of analytical grade.

Methods

Incorporation of Plasmid DNA Into Liposomes

The dehydration-rehydration procedure (Kirby and Gregoriadis, 1984) was used for the incorporation of pGL2 plasmid DNA into liposomes. In short, 2 ml of small unilamellar vesicles (SUV) composed of PC (16 μmoles) and DOPE (molar ratio 1:1); PC(16 μmoles), DOPE and PS (molar ratios 1:1:0.5; negatively charged); PC (16 μmoles), DOPE and SA, or BisHOP (molar ratios 1:1:0.5; positively charged); PC (16 μmoles), DOPE and DOTMA (molar ratios 1:1:0.25; positively charged); and DOPE (16 μmoles) and DOTMA (molar ratio 1:0.25; positively charged) were prepared as described (Kirby and Gregoriadis, 1984), mixed with 10-100 μg (10-100 μl) pGL-2 into which tracer $^{35}$S-labelled plasmid DNA pGL2 ($6 \times 10^4$–$7 \times 10^4$ dpm) had been added, and freeze-dried overnight. Following controlled (Kirby and Gregoriadis, 1984) rehydration and the generation of multilamellar (Gregoriadis et al, 1993) dehydration-rehydration vesicles (DRV), these were centrifuged at 40,000×g for 25 min to remove non-incorporated DNA. The liposomal pellets were suspended in 0.1 M sodium phosphate buffer supplemented with 0.9% NaCl, pH 7.2 (PBS) and centrifuged again. The washed pellets were re-suspended in PBS and stored at 4° C. until further use. In separate experiments, DNA-incorporating DRV as above in mixture with free, non-incorporated DNA (ie. before centrifugation), were microfluidized (Gregoriadis et al, 1990) in a Microfluidizer M110S (Microfluidics, Newton, Mass., USA) for 3 cycles or for 1, 2, 3, 5 and 10 cycles (PC:DOPE-:DOTMA liposomes only). Separation of incorporated DNA from free DNA in microfluidized liposomes was carried out by centrifugation as above (1, 2, 3 and 5 cycles) or molecular sieve chromatography (10 cycles) using (Gregoriadis et al, 1990) a Sepharose 4B CL column (Pharmacia). In some experiments, preformed (DNA-free) DRV were mixed with 10 or 50 μg DNA and either incubated at 20° C. for 20 h or microfluidized for 3 cycles. In both cases, liposomes were centrifuged as above to separate adsorbed from non-adsorbed DNA. DNA incorporation into liposomes or adsorption onto their surface was estimated on the basis of $^{35}S$ radioactivity recovered in the suspended pellets (non-microfluidized DRV and DRV microfluidized for 1,2,3 or 5 cycles) or the eluted fractions following chromatography (10 cycles).

Photon Correlation Spectroscopy

The z-average mean size of non-microfluidized and microfluidized DRV was measured in a Malvern Autosizer IIc as described elsewhere (Gregoriadis et al, 1993; Gregoriadis et al, 1990).

Incubation of Liposomes with Deoxyribonuclease

Non-microfluidized or microfluidized (3 cycles) DRV incorporating pGL2 plasmid DNA (0.75-22.5 µg) and tracer $^{35}S$-labelled pGL2 plasmid DNA in 1 ml PBS were mixed with 100 units deoxyribonuclease I, and incubated at 37° C. for 10 min. The reaction was stopped with 1 µl of 0.5 M EDTA (pH8) and the mixtures were centrifuged to separate digested from non-digested liposomal DNA. Digested DNA was estimated on the basis of released radioactivity in the supernatants. Preliminary work had established complete degradation of 100 µg naked pGL2 under identical conditions. In other experiments, samples of similar liposomes containing 2 µg DNA were diluted to 100 µl with a buffer containing 50 mM dithiothreitol and 50 µg/ml bovine serum albumin (fraction V; Sigma Chemical Co.), mixed with one unit of RQ1 deoxyribonuclease (Promega) and incubated at 37° C. for 30 min. Digestion was terminated by the addition of 1 µl 0.5 M EDTA (pH 8.0).

Agarose-gel Electrophoresis

Samples of non-microfluidized or microfluidized DNA-incorporating DRV were incubated as above with or without RQ1 deoxyribonuclease and then extracted twice with a phenol-chloroform mixture to remove lipid material. DNA in the aqueous layer was precipitated with ethanol, re-suspended in 20 µl TE buffer (10 mM Tris-Cl, pH 8.0 and 1 mM EDTA, pH 8.0) and subjected to agarose gel electrophoresis to determine DNA integrity.

Transfection Experiments

Monkey kidneys COS-7 epithelial cells maintained in Dulbecco's modified Eagle medium (DMEM) with 200 mM FLUTAMAX I (Gibco BRL) containing 10% foetal calf serum, were harvested by trypsinization, seeded in 24-well plates (Falcon) ($5\times10^4$ cells per well) and incubated for 18 to 24 h. Wells containing adherent cells at 70-80% confluency were washed with Dulbecco's phosphate buffered saline (without calcium or magnesium), pH7.2 (Gibco BRL) and then transfected with 1 µg (6-18 µl) liposome-incorporated or LipofectAMINE (24 µg lipid approximately) complexed with 1 µg pGL2 DNA in a volume of 0.5 ml OptiMEM 1 reduced serum medium containing GLUTAMAX I. Following incubation at 37° C. for four to six hours, the transfection medium was removed and replaced with 1 ml DMEM complete medium. Cells were incubated for a total of 48 h, lysed by scrapping into 200 µl of reporter lysis buffer (Promega) (cell lysis was enhanced by one cycle of freeze-thawing on dry ice) and then centrifuged at 12,000×g for 5 min to obtain clear supernatants. These were assayed in triplicates for luciferase activity with the luciferase assay system kit using an LKB 1251 luminometer with total light emission being recorded over 60 s. The protein concentration in each of the lysates was measured by the method of Bradford (1976) using the Bio-Rad protein assay solution. Luciferase activity was expressed as relative light units per mg of protein (RLU/mg).

Results

Incorporation of Plasmid DNA Into Liposomes

Plasmid DNA was incorporated into neutral DRV (710-843 nm diameter; Examples 1.1. (1-6) composed of PC and DOPE, a phospholipid reputed (Legendre and Szoka, 1995) to facilitate transfection, and in similar liposomes supplemented with negatively (590-871 nm; Examples 1.2. (1-5) or positively (647-899 nm; Examples 1.3. (1-6), 1.4. (1-4) and 1.5 (1-2) charged amphiphiles. Charged vesicle bilayer surfaces are known (Bangham et al, 1974) to contribute to larger aqueous spaces in between bilayers and, thus, to greater solute entrapment. In the case of the negatively charged DNA, further improvement of incorporation in positively charged liposomes (cationic DRV) would be expected as a result of electrostatic interactions. Table 1 shows that incorporation of DNA in neutral DRV was considerable (44-55%), and in negatively charged DRV still more so (45-63%) for each of the amounts used (10-100 µg) (Examples 1.1.(1-6) and 1.2.(1-5)). Moreover, the possibility that most of the DNA was adsorbed onto the liposomal surface rather than incorporated within the vesicles, was thought unlikely: incubation of preformed DRV with naked DNA resulted in only a modest proportion (12-13%) of it being recovered with the DRV on centrifugation (Examples 1.1.7 and 1.2 (6-7)). Microfluidization (3 cycles) of similar DNA-incorporating DRV in the presence of non-incorporated (free) DNA resulted in smaller (209-329 nm diameter) vesicles with a DNA content that was considerably reduced (to 10-20%) in the case of neutral DRV and to a lesser extent (to 37-51%) for negatively charged liposomes (Examples 1.1.(1-6) and 1.2.(1-5). Again, very little (6 and 10%) DNA was recovered with liposomes when preformed DRV were microfluidized in the presence of free DNA (Examples 1.1.7 and 1.2.(6-7)).

As anticipated, incorporation of DNA in cationic SA, BisHOP and DOTMA DRV was even greater (62-92%) with values remaining high (50-83%) for microfluidized DRV (269-383 nm; Examples 1.3.(1-6), 1.4.(1-4) and 1.5.(1-2)). Here, however, after incubation or microfluidization of preformed cationic DRV (SA) with naked DNA, as much as 40-60% of the material used was recovered with the liposomes, presumably as vesicle-surface bound (Examples 1.3(7-9)).

Incubation of Liposomal DNA with Deoxyribonuclease

Table 1 reveals that most of the DNA incorporated in neutral (45-72%), negatively charged (58-69%) or cationic (68-86%) liposomes was not degraded by DNase. In contrast, recovery of DNA adsorbed to the surface of neutral or negatively charged after exposure to the enzyme was low (18%) (Examples 1.1.7 and 1.2.6). With DNA adsorbed to the surface of cationic (SA) liposomes, however, a considerable proportion (41-58%) of the latter was not available for degradation by DNase (Examples 1.3. (7-8)). This may be attributed to a condensed DNA state known to occur with cationic vesicles and to be resistant to DNase (Legendre and Szoka, 1995). In view of these findings, the extent of DNA incorporation within the cationic liposomes (as opposed to that bound to their surface) at the end of the incorporation procedure is difficult to estimate accurately.

Results of liposomal DNA vulnerability to DNase were largely confirmed in experiments where samples of naked or liposomal DNA were exposed to RQ1 deoxyribonuclease and subsequently subjected to agarose gel electrophoresis. On the basis of intensity of staining and the appearance of smearing, it can be seen that, whereas naked plasmid DNA was completely digested, DNA entrapped within cationic liposomes was fully protected. DNA in neutral and negatively charged DRV, on the other hand, was less well protected as assessed by the lighter bands in the DNase digested samples compared to the undigested ones.

failed to show significant luciferase activity (results not shown), which can be explained by the microfluidization-induced progressive smearing of DNA.

It appears that of all the DRV preparations tested, positively charged SA and DOTMA DRV were more efficient than the remainder, with the microfluidized preparation (DOTMA) exhibiting the highest values of transfection. However, even this preparation was 10-15 fold less efficient than the control LipofectAMINE.

TABLE 1

| Example | Liposomes | 'E' ntrapped or 'C' omplexed | DNA used (µg) | % incorporated DNA (% retained DNA) DRV | Microfluidized DRV |
|---|---|---|---|---|---|
| 1.1.1 | PC:DOPE | E | 10 | 40.4 (71.9) | 12.5 (49.8) |
| 1.1.2 | PC:DOPE | E | 20 | 43.8 (62.0) | 17.3 (48.1) |
| 1.1.3 | PC:DOPE | E | 25 | 41.1 (67.1) | 16.9 (48.0) |
| 1.1.4 | PC:DOPE | E | 30 | 39.5 (60.0) | 20.6 (42.4) |
| 1.1.5 | PC:DOPE | E | 50 | 41.3 (45.3) | 10.1 (44.0) |
| 1.1.6 | PC:DOPE | E | 100 | 55.4 | — |
| 1.1.7 | PC:DOPE | C | 10 | 12.1 (17.8) | 6.8 (10.2) |
| 1.2.1 | PC:DOPE:PS | E | 10 | 55.8 (69.1) | 44.6 (67.8) |
| 1.2.2 | PC:DOPE:PS | E | 20 | 61.2 (60.9) | 40.9 (66.1) |
| 1.2.3 | PC:DOPE:PS | E | 25 | 61.0 (58.2) | 42.3 (62.6) |
| 1.2.4 | PC:DOPE:PS | E | 50 | 45.5 (58.0) | 37.0 (67.1) |
| 1.2.5 | PC:DOPE:PS | E | 100 | 63.0 | 51.0 |
| 1.2.6 | PC:DOPE:PS | C | 10 | 12.0 (17.6) | 10.2 (9.8) |
| 1.2.7 | PC:DOPE:PS | C | 50 | 13.3 | 10.8 |
| 1.3.1 | PC:DOPE:SA | E | 10 | 64.1 (78.1) | 50.3 (63.1) |
| 1.3.2 | PC:DOPE:SA | E | 20 | 71.9 (75.0) | 65.5 (59.9) |
| 1.3.3 | PC:DOPE:SA | E | 25 | 82.3 (75.2) | 64.7 (58.2) |
| 1.3.4 | PC:DOPE:SA | E | 30 | 74.8 (70.1) | 56.2 (58.0) |
| 1.3.5 | PC:DOPE:SA | E | 50 | 71.2 (67.9) | 50.9 (57.4) |
| 1.3.6 | PC:DOPE:SA | E | 100 | 84.4 | 60.1 |
| 1.3.7 | PC:DOPE:SA | C | 10 | 59.7 (41.1) | 31.6 (40.2) |
| 1.3.8 | PC:DOPE:SA | C | 25 | 45.1 (58.5) | 12.9 (41.0) |
| 1.3.9 | PC:DOPE:SA | C | 50 | 40.3 | 16.3 |
| 1.4.1 | PC:DOPE:BH | E | 10 | 68.4 (75.3) | 51.9 (63.1) |
| 1.4.2 | PC:DOPE:BH | E | 20 | 70.8 (70.2) | 55.5 (64.0) |
| 1.4.3 | PC:DOPE:BH | E | 25 | 62.3 (69.9) | 52.2 (78.2) |
| 1.4.4 | PC:DOPE:BH | E | 50 | 75.6 | 62.1 |
| 1.5.1 | PC:DOPE:DOTMA | E | 50 | 81.0 (85.9) | 76.3 (79.1) |
| 1.5.2 | PC:DOPE:DOTMA | E | 100 | 92.6 | 83.2 |

BH = BisHOP

Transfection with Liposomal pGL2 Plasmid DNA

In experiments where COS-7 cells were transfected with pGL2 plasmid DNA incorporated in non-microfluidized DRV liposomes or complexed with LipofectAMINE, the latter serving as a control, significant levels of luciferase activity over background were observed with each of the DRV formulations. However, levels of activity with cationic DRV (DOPE:DOTMA, PC:DOPE:DOTMA and PC:DOPE:SA) were approximately 10-fold higher than those achieved with neutral (PC:DOPE) and negatively charged (PC:DOPE:PS) and also the cationic PC:DOPE:BisHOP liposomes (Table 2). As the size of liposomes may be related to the efficiency of transfection, related experiments were also carried out with DNA incorporated in DRV which were microfluidized for 1,2,3,5 or 10 cycles to produce vesicles of progressively smaller size (386, 319, 262, 235 and 123 nm z-average diameter respectively; not shown). Table 2 indicates that microfluidization (3 cycles) of the PC:DOPE:DOTMA DRV improved their transfection efficiency by 10-fold. However, transfection experiments with PC:DOPE:DOTMA, DOPE:DOTMA, PC:DOPE and PE:DOPE:PS liposomes subjected to 5 or 10 cycles of microfluidization

TABLE 2

Luciferase activity in transfected cells

| Example | Liposomes | Luciferase activity RLU/mg |
|---|---|---|
| 1.6.1 | DOPE:DOTMA | $1.5 \times 10^4$ |
| 1.6.2 | PC:DOPE:DOTMA | $1.3 \times 10^4$ |
| 1.6.3 | PC:DOPE:DOTMA Mf × 3 | $7 \times 10^4$ |
| 1.6.4 | PC:DOPE:BisHOP | $2 \times 10^3$ |
| 1.6.5 | PC:DOPE:SA | $9 \times 10^3$ |
| 1.6.6 | PC:DOPE | $2 \times 10^3$ |
| 1.6.7 | PC:DOPE:PS | $3 \times 10^3$ |
| 1.6.8 | LIPOFECTAMINE | $3 \times 10^6$ |

Mf × 3 - microfluidized, 3 cycles.

EXAMPLE 2

Immune Response After in vivo Transfection

Using the materials as described and from the sources of Example 1 (and in addition 3β[N—(N'N'-dimethylaminoethane)-carbamyl]cholesterol, DC-CHOL, obtained from Dr C Kirby and DOTAP-1,2-dioleoyloxy-3-trimethylammonium propane) experiments were conducted to determine the immune response after in vivo transfection. The polynucleotide is plasmid DNA expressing the Hepatitis B surface antigen (S region, plasmid pRc/CMV-HBS of the ayw type (Davis H L et al)). Liposomes were formed in each case using 16 micromoles PC (12 mg) throughout, with the cationic lipid specified in the tables in the ratios used in the tables. Plasmid DNA was either entrapped into the liposomes (in the amount specified in the table) using the methods of example 1, or complexes of preformed cationic liposomes and DNA were made, by mixing those components together in aqueous suspension (using techniques comparable to the prior art by Eppstein, mentioned above).

Liposomes with entrapped DNA, the complexes and naked DNA were then administered to mice for the in vivo transfection experiments. Balb/c mice, in groups of three or four, were injected intramusuclarly (hind leg) with the preparations in an amount such as to adminster the amount of DNA shown in table 4. Plasmid DNA was either entrapped into the liposomes (in the amount specified in the table) using the methods of example 1, or complexed with preformed cationic liposomes and DNA, by mixing those components together in aqueous suspension (using techniques comparable to the prior art by Eppstein, mentioned above).

Liposomes with entrapped DNA, the complexes and naked DNA were then administered to mice for the in vivo transfection experiments. Balb/c mice, in groups of three or four, were injected intramuscularly (hind leg) with the preparations in an amount such as to administer the level of DNA specified in table 4. For each test, the amount of lipid in the liposome preparation administered to the mice is approximately constant and is a value in the range 1-2 mg total PC lipid.

Subsequently mice were bled and the sera were tested by ELISA techniques to determine the immune response. In these in vivo experiments, the ELISA test is carried out as described by Davis et al (1987) using the S region antigen of ayw Type Hepatitis B. Tests were used to determine anti-HBS Ag (S region ayw type)-$IgG_1$, $IgG_{2a}$ and $IgG_{2b}$. The immune responses obtained are expressed as $log_{10}$ (mean + or − standard deviation) of serum dilutions required to give an absorbance reading (in the horseradish peroxidase ELISA test) of about 0.200.

In the experiments the results of which are reported in table 4, the mice were injected on days 0, 10, 20, 27 and 37 and were bled on days 26, 34 and 44. In the results given in table 5, the mice were injected on days 0, 7, 14, 21 and 28 and were bled on days 21 and 28.

Results and Conclusions

TABLE 3

Entrapment of plasmid DNA (into liposomes).

| Example | Liposomes (molar ratio) | Entrapped or complexed | DNA used (μg) | Entrapment/ complexation rate (% of DNA used) |
|---|---|---|---|---|
| 2.1 | PC, DOPE (1:0.5) | E | 100 | 57.3 |
|  |  | E | 150 | 53.6 |
| 2.2 | PC, DOPE, DC-CHOL (1:0.5:0.25) | E | 100 | 95.4 |
|  |  | E | 150 | 78.9 |
| 2.3 | PC, DOPE, DOTAP (1:0.5:0.25) | E | 100 | 82.9 |
|  |  | E | 100 | 78.4 |
|  |  | E | 150 | 77.1 |
|  |  | E | 150 | 82.1 |
| 2.4 | PC, DOPE, DOTAP (1:0.5:0.25) | C | 100 | 93.9 |
|  |  | C | 150 | 83.3 |

TABLE 4

Immune response * (ELISA results ± SD) of mice immunised with free or liposome entrapped DNA.

| Lipids, ratios preparation (example) | Injected DNA (ug) | 26 days | | | 34 days | | | 44 days | | |
|---|---|---|---|---|---|---|---|---|---|---|
| | | $IgG_1$ | $IgG_{2a}$ | $IgG_{2b}$ | $IgG_1$ | $IgG_{2a}$ | $IgG_{2b}$ | $IgG_1$ | $IgG_{2a}$ | $IgG_{2b}$ |
| PC, DOPE, DOTAP (2.3) (1.0:0.5:0.25 | 5 | 3.1 ± 0.2 | 2.2 | ND | 4.2 ± 0.4 | 3.2 ± 0.0 | 3.1 ± 0.2 | 5.5 ± 0.2 | 3.1 ± 0.3 | 2.7 ± 0.0 |
| | 10 | 3.2 ± 0.0 | ND | ND | 4.2 ± 0.0 | 3.2 ± 0.0 | 3.2 ± 0.0 | 4.8 ± 0.5 | 3.4 ± 0.3 | 3.0 ± 0.3 |
| PC:DOPE: DC-CHOL (2.2) (1.0:0.5:0.25 | 5 | 3.0 ± 0.3 | 2.2 | ND | 4.0 ± 0.2 | 3.0 ± 0.3 | 2.7 ± 0.0 | 5.2 ± 0.2 | 3.0 ± 0.3 | 2.9 ± 0.3 |
| | 10 | 3.0 ± 0.3 | ND | ND | 4.0 ± 0.2 | 3.6 ± 0.2 | 3.1 ± 0.2 | 5.0 ± 0.2 | 3.4 ± 0.3 | 3.2 ± 0.0 |
| Naked DNA | 5 | 2.2 ± 0.0 | ND | ND | 2.2 ± 0.0 | 2.2 ± 0.0 | 1.8 ± 0.0 | 3.2 ± 0.0 | 2.2 ± 0.0 | 2.2 ± 0.0 |
| | 10 | 2.4 ± 0.2 | ND | ND | 2.2 ± 0.0 | 2.2 ± 0.0 | 1.8 ± 0.0 | 2.9 ± 0.3 | 2.2 ± 0.0 | 2.2 ± 0.0 |

ND means "not determined"
* log 10 of dilutions needed to give a reading of about 0.200 in the ELISA test.
See also FIG. 1 in which A represents the results of the liposomes including DOTAP, B the results of liposomes including DC-Chol, C the results of liposomes including stearylamine in the same amount (not shown in the table) and D naked DNA, in each case for the case where 5 μg DNA is administered. White bars are $IgG_1$ values, black bars are $IgG_{2a}$ and dotted bars are $IgG_{2b}$.

TABLE 5

Immune response (ELISA results ± SD) of mice immunised with naked, complexed and entrapped DNA

| DNA preparation (example) | Test Report | Injected DNA (ug) | 21 days IgG$_1$ | P | 28 days IgG$_1$ | P |
|---|---|---|---|---|---|---|
| PC, DOPE, DOTAP 1.0:0.5:0.25 (entrapped) (2.3) | a | 1 | 2.2 ± 0.0 | | 2.5 ± 0.3 | a vs g <0.05 |
| | b | 10 | 3.2 ± 0.0 | b vs a, c, d, e, f, g, h <0.0001 | 4.0 ± 0.2 | b vs h <0.0007 |
| PC, DOPE DOTAP 1.0:0.5:0.25 (complexed) (2.4) | c | 1 | 2.2 ± 0.0 | | 2.4 ± 0.2 | |
| | d | 10 | 2.2 ± 0.0 | | 2.8 ± 0.2 | d vs b <0.0032 |
| PC, DOPE (2.1) 1.0:0.5 | e | 1 | 2.2 ± 0.0 | | 2.2 ± 0.0 | |
| | f | 10 | 2.2 ± 0.0 | | 2.7 ± 0.0 | f vs b <0.001 f vs h <0.003 |
| Naked DNA | g | 1 | 2.2 ± 0.0 | | 2.2 ± 0.0 | |
| | h | 10 | 2.2 ± 0.0 | | 2.2 ± 0.0 | h vs d <0.0001 |

In the tables the columns P show the result of students paired t-test indicating the confidence level that the results, as specified, are different from one another.

Table 3 shows that the percentage entrapment is extremely high for lipid compositions containing cationic lipids. The complexation rate of plasmid DNA with preformed lipids is also very high. In each case, the percentage entrapment/complexation rate is little effected by the use of 100 μg or 150 μeg of DNA.

Figure 1:
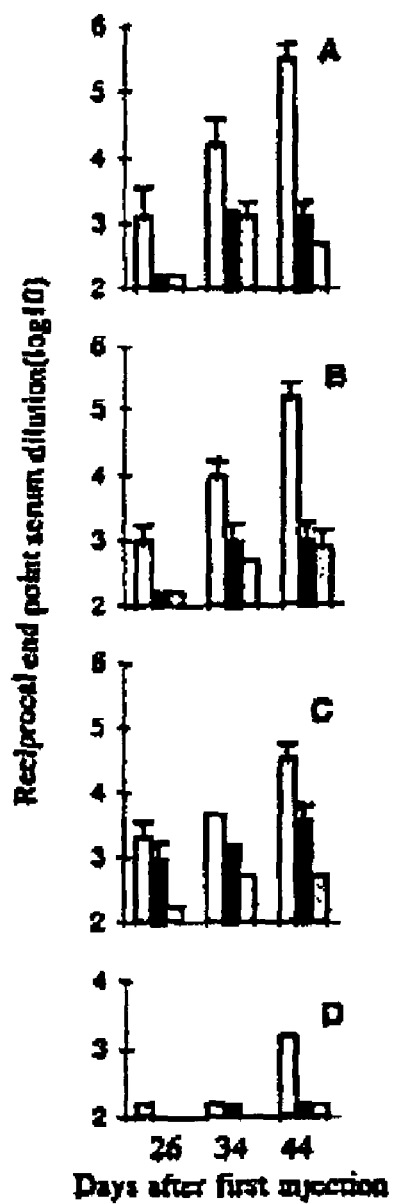
FIG. 1 is a series of bar charts showing the results mentioned in Example 2, table 4.

Table 4 and FIG. 1 show that the immune response following immunisation of mice with entrapped DNA encoding Hepatitis B surface antigen is much higher than following immunisation with naked DNA. Whilst this effect is already apparent after 26 days from the start of the experiment, the effect becomes yet more pronounced as the experiment continues. The effect is particularly pronounced for IgG$_1$ although the levels of both IgG$_{2a}$ and IgG$_{2b}$ are also present in increased amounts as compared to naked DNA transmission, after all bleeds.

The results in table 5 show that for naked DNA, no response is seen even after 28 days following the first administration of DNA.

For DNA entrapped within neutral liposomes (PC, DOPE) there is no increase in immune response at 21 days although there is slight increase in response for the higher amount of injected DNA after 28 days and this is significantly higher than the response after administration of when naked DNA.

For the complex of preformed cationic liposomes and DNA, the immune response does appear to be developing after 28 days from the start of the experiment, for both levels of DNA administration and is significantly higher than the response after administration of naked DNA. However the immune responses are not as high as those obtained for the DNA entrapped within cationic liposomes.

For cationic liposomes with entrapped DNA after 21 days, already the immune response is significantly higher than all of the other examples, where the amount of DNA injected is 10 μg; though there is no significant difference between the response after administration of 1 μg DNA entrapped in cationic liposomes and any of the other examples in which 1 μg DNA is administered. After 28 days, with the lower level of DNA administered (1 μg) there is a significantly increased immune response as compared to high or low amounts of naked DNA. However there is no significant difference to the response following administration of the lower levels of DNA complexed with cationic liposomes or entrapped in neutral liposomes. For the higher level of DNA administered (10 μg) entrapped in cationic liposomes, after 28 days the immune response is significantly higher than all of the other tests.

EXAMPLE 3

Cytokine Levels in the Spleens of Mice Immunized with Naked, Complexed or Liposome Entrapped Plasmid DNA Balb/c mice in groups of four (the same protocol and experiment as example 2) were injected intramuscularly on days 0.7, 14, 21 and 28 with 1 (white bars) or 10 μg (black bars) of pRc/CMV HBS entrapped in positively charged liposomes composed of PC, DOPE and DOTAP (A), uncharged liposomes composed of PC and DOPE (B), complexed with similar performed cationic DOTAP liposomes (C) or in naked form (D). "Control" represents cytokine levels in normal unimmunized mice. Three weeks after the final injection, mice were killed and their spleens subjected to cytokine analysis. Endogenous levels of IFN-γ and IL-4 in the spleen were determined by the method of Nakane et al as previously modified by de Souza et al. Individual spleens were weighed, homogenized in ice-cold RPMI containing 1% 3-[(cholamidopropyl)dimethylammonio]-1-propanesulphonate (CHAPS; Sigma) in a Dounce tissue homogenizer and 10% (wt/vol) homogenates were prepared. Homogenates were left on ice for 1 h and insoluble debris were then removed by centrifugation at 2000×g for 20 min. The clear supernatants were stored at −70° C.

Cytokine Assays

Figure 2:
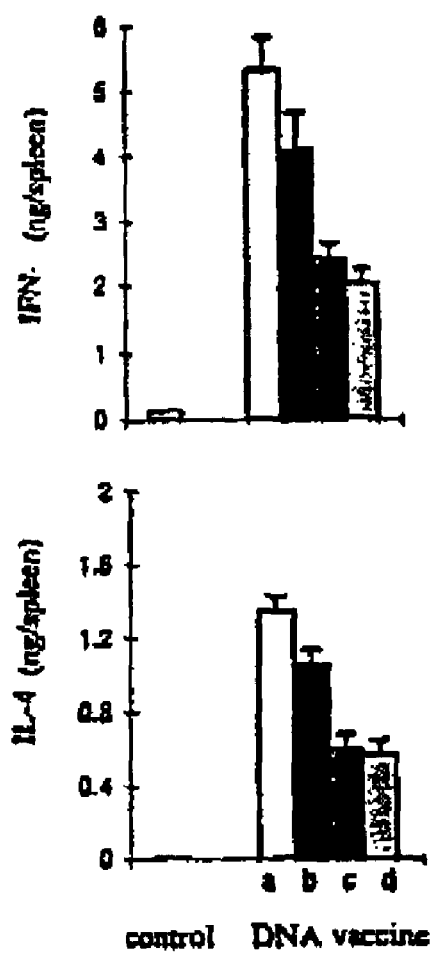
FIG. 2 is a series of bar charts showing the results of example 3.

Standard capture ELISAs were used with monoclonal antibody pairs and Maxisorp (NUNC, UK) plates. Primary monoclonal antibodies against IFN-γ (R46A2) and IL-4 (11B11) and secondary biotinylated anti-mouse IL-4 (BVD6-24G2) and anti-mouse IFN-γ (XMG1.2) monoclonal antibodies (Pharmingen, USA) were used with streptavidin peroxidase (Dako, Denmark) and o-phenylenediamine (Sigma) as substrate. Recombinant IFN-γ and IL-4 standards were from Pharmingen. Results (mean±SE) are expressed as ng/spleen from at least 4 mice. The results are shown in FIG. 2 in which each bar represents the mean±SE of a group of 4 mice (a-d representing the liposomes as specified above).

The data (FIG. 2) show that activation for both Th1 and Th2 subsets was greater with liposome-entrapped DNA when compared with naked or complexed DNA. This finding was also confirmed in preliminary T cell proliferation assays against the HBsAg antigen in vitro. It therefore appears that immunization with liposome-entrapped plasmid DNA induces both humoral and cell-mediated immunity.

EXAMPLE 4

Immune Responses in Mice After a Single Injection of Plasmid DNA

Most reports on naked DNA vaccination have employed protocols of multiple injections but a single dose also produces a humoral response to the encoded antigen (Davis et al Human Gene Therapy 1993, and Raz et al PNAS 1994). For instance, total IgG response for the naked pRc/CMV HBS (identical to the plasmid used here) was detectable 1-2 weeks after injection, to reach peak values by 4-8 weeks (Davis et al 1996).

Balb/c mice in groups of four were injected once intramuscularly with 2 (white bars see FIG. 3) or 10 µg (black bars) of pRc/CMV HBS entrapped in positively charged liposomes composed of PC, DOPE and DOTAP (A), uncharged liposomes composed of PC and DOPE (B), complexed with preformed similar DOTAP liposomes (C) or in the naked form (D). Anti-HBsAg $IgG_1$ responses were analysed (ELISA) in sera obtained at time intervals after injection. Immune responses were mounted by all mice injected with liposomal DNA but became measurable only at 20-27 days. The remaining details were as in example 2. Differences in $\log_{10}$ values (both doses; all time intervals) between mice immunized with cationic liposomal DNA and mice immunized with naked DNA were statistically significant ($P<0.0001$-$0.002$). In a fifth group of four mice immunized once as above with 10 µg pRc/CMV HBS entrapped in anionic liposomes composed of PC, DOPE and PS (made by the method as described in Example 1), $IgG_1$ responses ($\log_{10}$) were $2.25\pm0.0$ and $2.73\pm0.0$ at 21 and 29 days respectively.

Figure 3:
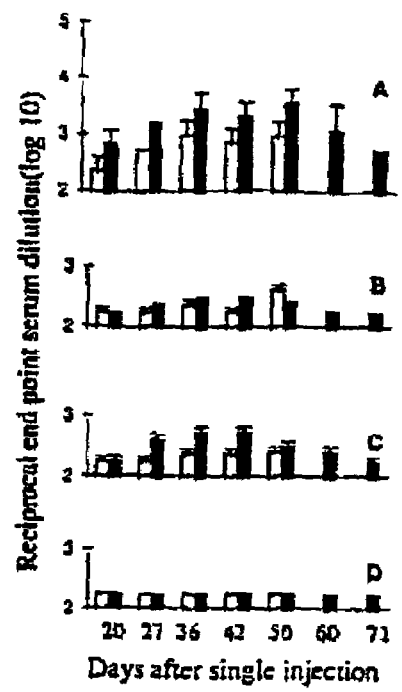
FIG. 3 is a series of bar charts showing the results of example 4.

Under the present conditions of single immunization (FIG. 3) with much lower doses of pRc/CMV HBS (2 and 10 µg), anti-HBsAg $IgG_1$ response for naked and complexed DNA was barely detectable even by seven weeks. In contrast, there was an early and pronounced $IgG_1$ response for DNA entrapped in cationic liposomes and a delayed but significant response for DNA entrapped in neutral or negatively charged liposomes (FIG. 3).

EXAMPLE 5

Humoral and Cell-mediated Response of In-bred and Out-bred Mice Injected with Hep B Antigen in Cationic Liposomes Groups of mice (4-5 animals per group) were injected (i.m., i.p., i.v. or s.c.) twice (on days 0 and 7) with 10 µg pRc/CMV HBS (encoding the S region of hepatitis B surface antigen; subtype ayw) entrapped in cationic DRV liposomes composed of egg phosphatidylcholine (PC), dioleoyl phosphatidylcholine (DOPE) and 1,2-dioleoyl-3-(trimethylammonium)propane (DOTAP) (molar ratios 1:5.5:0.25) (produced using the general techniques and materials described above in example 1), or with 10 µg of naked pRc/CMV HBS (both in PBS). Animals were bled at time intervals and $IgG_1$, $IgG_{2a}$, and $IgG_{2b}$ were measured by ELISA in the plasma. At the end of the experiment (38 days after the first injection) animals were killed and the cytokines IFNγ and IL-4 were measured in the spleen as described (for additional experimental details see Gregoriadis et al, 1997). The cytokines were also measured in the spleen of control (intact) mice.

Results

Figure 5:
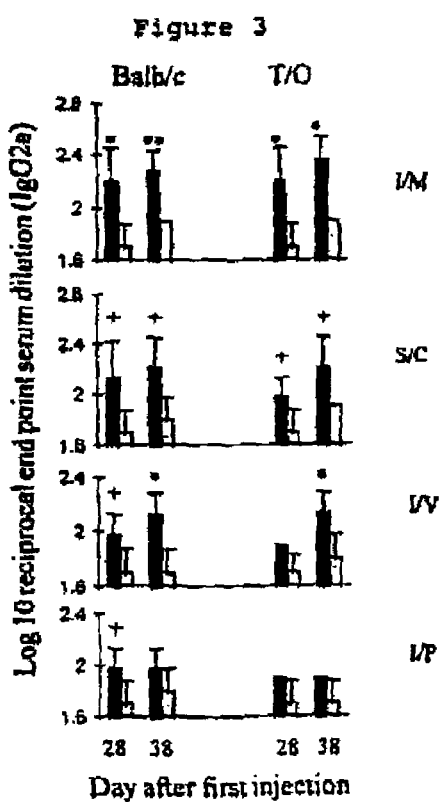
FIGS. 4 to 8 are a series of bar charts showing the results of example 5.
Figure 4:
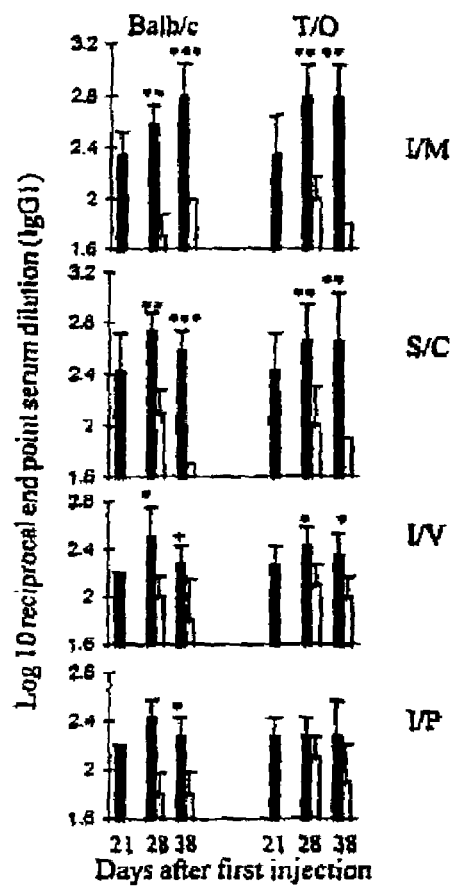
Figure 6:
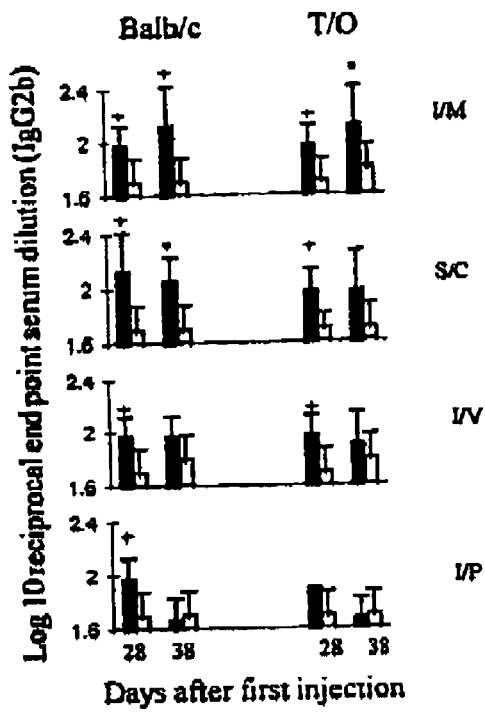

Results show that immune responses (mean±SD) for both strains of mice became measurable only after 21 ($IgG_1$; FIG. 4) or 28 days ($IgG_{2a}$ and $IgG_{2b}$; FIGS. 5 and 6 respectively) after the first injection. Responses for liposomal DNA (black bars) were generally significantly greater than those for naked DNA (dotted bars) (both strains and all routes, especially im, sc and iv). Significant levels ($P<0.05$) increase in the order of +*,,*.

Figure 7:
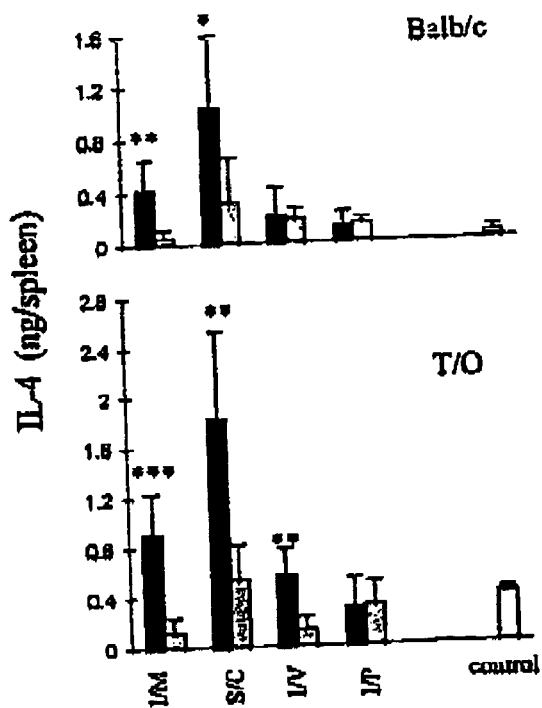
Figure 8:
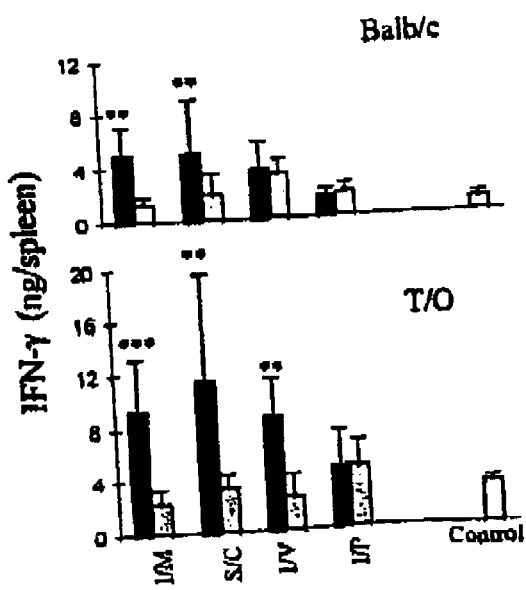

Analysis of the cytokines IFNγ (Th1 response) (FIG. 7) and interleukin 4 (IL-4) (Th2 response) (FIG. 8) revealed significantly greater levels for liposomal DNA by the im and sc routes in both strains for the (iv route in T/o mice). There was no difference in values between liposomal and naked DNA for the ip route (both strains).

The relationship between murine anti-HBs endpoint titers and milli-international units/ml (mIU/ml, as defined by the World Health Organization plus inferred protective efficacy in man is expressed in:—Brazolot. Millan Cl., Weeratna R, Krieg A M, Siegrist C A, Davis I I L. Proc Natl Acad Sci USA Dec. 22, 1998; 95(26):15553-8.

"Endpoint titers were defined as the highest plasma dilution that resulted in an absorbance value (OD450) two times greater than that of nonimmune plasma, with a cut-off value of 0.05, and seroconversion was defined as a dilution titer>100. The relationship between endpoint titers and those in milli-international units/ml (mIU/ml), as defined by the World Health Organization, was determined to be very close to 1:1 by comparing a panel of mouse plasma against human-derived standards (Monolisa Anti-HBs "Standards," Sanofi Diagnostics Pasteur, Montreal, Canada) using a non-species-specific conjugate (Monolisa Anti-HBs Detection Kit, Sanofi Diagnostics Pasteur). A titer of 10 mIU/ml is considered protective against HBV infection in humans."

Thus using similar reasoning it is reasonable to propose that if the liposomal entrapped DNA (Hepatitis B) vaccine produced similar immune responses in man to that obtained in mice, we would achieve protective efficacy.

EXAMPLE 6

Entrapment Value for Six Different Plasmid DNA's $^{35}$S-labelled plasmid DNA (10-500 µg) was incorporated into or mixed with neutral, anionic or cationic dehydration rehydration vesicle (DRV) using the technique described in example 1. The plasmid DNAs used were the following:

pGL2—encoding luciferase, as for example 1 pRc/CMV HBS—hepatitis B surface antigen (S) region as in example 2

PRSVGH—encoding human growth hormone, a therapeutic protein pCMV4.65—micobacterium leprosy protein, an antigen pCMV4.EGFP—"fluorescent green protein"

VR1020—schistosome protein, an antigen.

The lipids used included neutral lipids PC and DOPE described in example 1 above, anionic lipids, PS, phosphatidyl serine, described in example 1 or phosphatidyl glycerol (PG) and cationic compounds stearylamine (SA), BisHOP and DOTMA, all described in example 1, DC-Chol and DOTAP, as used in example 2 and, in addition 1,2-dioleoyl-3-dimethylammonium propane DODAP.

The table below indicates whether the plasmid DNA was incorporated (that is encapsulated into (a) or merely admixed (b) with the DRV). The table further indicates the lipid components and the incorporation values for DNA. Previous tests had shown that incorporation values using different amounts of DNA for each of the DRV formulations did not differ significantly. Results were therefore pooled and the values shown in the table are means of values obtained from 3 to 5 experiments.

TABLE 6

Incorporation of plasmid DNA into liposomes

Incorporated plasmid DNA (% of used)

| Liposomes | pGL2 | pRc/CMV HBS | pRSVGH | pCMV4.65 | pGMV4.EGFP | VR1020 |
|---|---|---|---|---|---|---|
| PC, DOPE[a] | 44.2 | 55.4 | 45.6 | 28.6 | | |
| PC, DOPE[b] | 12.1 | | 11.3 | | | |
| PC, DOPE, PS[a] | 57.3 | | | | | |
| PC, DOPE, PS[b] | 12.6 | | | | | |
| PC, DOPE, PG[a] | | | 53.5 | | | |
| PC, DOPE, PG[b] | | | 10.2 | | | |
| PC, DOPE, SA[a] | 74.8 | | | | | |
| PC, DOPE, SA[b] | 48.3 | | | | | |
| PC, DOPE, BisHOP[a] | 69.3 | | | | | |
| PC, DOPE, DOTMA[a] | 86.8 | | | | | |
| PC, DOPE, DC-Chol[a] | | 87.1 | 76.9 | | | |
| PC, DOPE, DC-Chol[b] | | | 77.2 | | | |
| PC, DOPE, DOTAP[a] | | 80.1 | 79.8 | 52.7 | 71.9 | 89.6 |
| PC, DOPE, DOTAP[b] | | 88.6 | 80.6 | 67.7 | | 81.6 |
| PC, DOPE, DODAP[a] | | | 57.4 | | | |
| PC, DOPE, DODAP[b] | | | 64.8 | | | |

The results show that, by encapsulating the DNA, far higher values for the level of incorporation can be achieved where the lipid is negatively charged. Where cationic lipid is used, the incorporation values do not appear to differ significantly between encapsulation and physical admixture, although it seems that encapsulation gives higher values where the cationic component is a non-lipidic compound (stearylamine).

EXAMPLE 7

The Effective Lipid Composition of Cationic Liposomes on the Immune Response to the HBsAg Antigen Encoded by the Entrapped pRc/CMV HBS Using the general techniques described above, plasmid DNA was entrapped into various cationic liposomes. The lipids used and the molar ratios are shown in table 7 below. The lipids were as used in previous examples and additional PE is phosphatidyl ethanolamine with egg lipid, and DSPC, di-stearoylphosphatidylcholine, a saturated lipid. Balb/c mice were injected intramuscularly in groups of 5 with 10 μg of free or liposome entrapped plasmid on day zero, two weeks and five weeks. Animals were bled at 8, 10 and 13 weeks and sera assayed by ELISA for anti-HBsAg (S region) $IgG_1$ antibodies. The technique used is as generally described in example 5. The results are shown in Table 7 below.

TABLE 7

| Liposomes mole ratios of lipids | $IgG_1$ response ($\log_{10}$ reciprocal end point dilution ± SD) | | |
|---|---|---|---|
| | 8 weeks | 10 weeks | 13 weeks |
| A. PC:DOPE:DOTAP (1:0.5:0.25) | 2.99 ± 0.24 | 2.87 ± 0.29 | 2.63 ± 0.15 |
| B. PC:PE:DOTAP (1:0.5:0.25) | 2.99 ± 0.56 | 3.17 ± 0.64 | 2.75 ± 0.35 |
| C. PC:DOTAP (1:0.25) | 2.05 ± 0.66 | 1.98 ± 0.58 | 1.83 ± 0.33 |
| D. DSPC:DOPE:DOTAP (1:0.50:0.25) | 2.51 ± 0.19 | 2.48 ± 0.19 | 1.90 ± 0.00 |

TABLE 7-continued

| Liposomes mole ratios of lipids | $IgG_1$ response ($\log_{10}$ reciprocal end point dilution ± SD) | | |
|---|---|---|---|
| | 8 weeks | 10 weeks | 13 weeks |
| E. PC:Chol:DOTAP (1:0.50:0.25) | 2.57 ± 0.35 | 2.51 ± 0.27 | 2.14 ± 0.23 |
| F. Free pRc/CMV HBS | 1.30 ± 0.00 | 1.30 ± 0.00 | 1.23 ± 0.13 |

Statistical analysis of the results (unpaired T-test) revealed significant differences between (a) all liposomal DNA formulations and free DNA (P<0.0001-0.0441; all time intervals), PC:DOPE:DOTAP and PC:DOTAP(P<0.0036-0.0357; all time intervals), PC:PE:DOTAP and PC:DOTAP (P<0.0095-0.0385; 10 and 13 weeks), PC:DOPE:DOTAP and DSPC:DOPE:DOTAP(P<0.0001-0.0138; 8 and 13 weeks) and PC:DOPE:DOTAP and PC:CHOL:DOTAP (P<0.0158; 13 weeks).

Results suggest that in terms of liposomal efficacy in promoting immune responses, (a) DOPE can be replaced by PE without loss of liposomal efficacy (DOPE and PE are both unsaturated lipids), b) phosphatidylethanolamine (PE or DOPE) renders liposomes more efficient than liposomes without this type of lipid, c) replacement of PC with the saturated DSPC reduces liposomal efficacy, d) liposomes with cholesterol but without phosphatidylethanolamine are nearly as effective as liposomes with phosphatidylethanolamine but only at 8 and 10 weeks.

EXAMPLE 8

Entrapment of pRc/CMV HBS into Non-phospholipid Liposomes

In this example various liposome forming components other than phospholipids were used to entrap the hepatitis antigen used in previous examples. The liposome forming components included a glyceride, MonoPal; 1-Monopalmitoyl-rac-glycerol, and nonionic surfactants, Span 60(-sorbitan monostearate) and Solulan 24, (a 24 mole ethoxylated complex of lanolin alcohols and related fatty alcohols).

(Span 60 and Solulan 24 are trademarks). The mole ratios of the liposome forming components are shown in the table. The other components are as used in the above examples.

The results show that adequate entrapment rates can be achieved using liposome forming components not including phospholipids. Nonionic surfactants, optionally in combination with other non phospholipid lipidic components such as cholesterol can give adequate entrapment rates. It was noted that liposomes formed in examples 8.4, 8.5, 8.6 and 8.8 precipitated on standing and were thus not optimised in terms of composition.

The entrapment rates are shown in Table 8 below.

TABLE 8

| Example | Liposomes | Molar Ratios (also absolute in terms μmole) | Entrapment (% of DNA used) |
|---|---|---|---|
| 8.1 | MonoPal:Chol:DOTAP | 16:16:4 | 63.2 |
| 8.2 | MonoPal:Chol:DOTAP | 20:8:4 | 84.0 |
| 8.3 | MonoPal:Chol:DOTAP | 16:8:4 | 64.1 |
| 8.4 | MonoPal:DOPE:DOTAP | 16:8:4 | 28.1 |
| 8.5 | MonoPal:Chol:DOPE:DOTAP | 16:16:8:4 | 46.4 |
| 8.6 | SPAN60:Chol:DOTAP | 16:16:4 | 83.6 |
| 8.7 | SPAN60:Solulan:Chol:DOTAP | 16:0:72:16:4 | 66.0 |
| 8.8 | SPAN60:Chol:DOTAP | 20:8:4 | 55.8 |

EXAMPLE 9

Material and Methods:

Lipids

Egg phosphatidylcholine (PC), Dioleoyl phosphatidylethanolamine (DOPE) and 1,2-dioleoyl-3-(trimethylammonium)propane (DOTAP) were purchased from Sigma Chemical Co., UK. All lipids were stored (−20° C.) dissolved in chloroform, purged with nitrogen.

DNA

Plasmid p1, 17/SichHA (ref DNA HA) was provided by Dr J. Robertson (NIBSC, UK) (Johnson, P et al. J. Gen. Virol. 2000, 1737-1745) containing the full length HA from influenza A/Sichuan/2/87. Both plasmids for dosing were commercially produced by Aldevron (Fargo, USA) and contained <100 Endotoxin Unit (EU)/mg of DNA with no residual protein detectable.

Preparation of Liposome Compositions

Briefly, small unilamellar vesicles (SUV) were prepared from egg phosphatidylcholine (PC, 16 μM) and dioleoyl phosphatidylcholine (DOPE, 8 μM) and 1,2-dioleoyloxy-3-(trimethylammonium)propane (DOTAP, 4 μM) (4:2:1 molar ratio) by sonication were mixed with DNA (100 μg) and freeze-dried overnight as described in (Gregoriadis, G. et al J Drug Targeting. 1996, 3(6), 467-475 and in Kirby, C., Gregoriadis, G. Biotechnology. 1994, 2,979-984). Following rehydration under controlled conditions, the generated dehydrated-rehydrated vesicles (DRV liposomes) were washed by centrifugation to remove non-incorporated DNA. The washed pellets were resuspended in PBS to the required dose volume. Formulations were prepared in tripliate, two vials for dosing (prime and boost) and one vial for % entrapment calculations consisted of radio labeled tracer ($^{35}$S HA DNA) added to the DNA to be entrapped DNA incorporation into the liposome was estimated on the basis of $^{35}$S (for DNA) radioactivity recovered in the suspended pellet.

Animal Procedures

Female Balb/c mice 6-12 weeks old (Harlan, UK) were immunised by subcutaneous injection administered in 0.2 ml dose. Group 1 mice received 10 μg of DNA (non entrapped) and Group 2 received 10 μg of DNA liposomally entrapped). Negative control mice received doses PBS respectively. Mice received two doses of antigen at days 0 and 28.

Splenocyte Cytokine Response

Animals were culled by cervical dislocation on day 15 after the second immunisation and their spleens isolated and processed individually for the preparation of spleen cells according to a protocol described elsewhere (Bacon et al, Journal of Liposome Research, 12 (1 & 2): 173-183, 2002). Splenocyte suspensions from each animal, prepared in IMDM (Invitrogen) supplemented with (50 IU -50 μg/ml Penicillin-Streptomycin (Sigma), Linoleic-Oleic-Albumin solution (Sigma) and 10 mg/l Apotransferrin (Sigma) were seeded at 2×10$^6$ cells/well in 24-well plates (NUNC) and stimulated with recall antigen which was no antigen 2 μg/ml of LPS-free [what is LPS-free?] inactivated Flu (Sichuan virus, 10 μg/ml of LPS-free inactivated Flu (Sichuan) virus, 10 μg/ml of inactivated Flu (Sichuan) virus or 10 μg/ml Lysozyme. After 72 hours incubation at 37° C., plates were spun at 150 g for 5 min at RT and the supernatant collected and analysed for IFN-γ and IL-4 production with OptEIA Elisa kits (PHARMINGEN) according to the manufacturer's instructions.

Results

The results are shown in FIGS. 9a-c. FIG. 9a shows the cytokine response for IFNγ for the cells from animals vaccinated test entrapped vaccines with the five test challenges. FIG. 9b shows the IFNγ response for the cells from animals vaccinated with naked DNA and 9c shows the IFNγ results for cells from animals vaccinated with PBS.

Liposomally entrapped DNA produces a significantly higher, p<0.05 for recall antigen LPS free-Flu and Flu (10 μg/ml), IFN-γ cytokine response to Flu influenza antigen than DNA alone.

[Why are the results for IL-4 not shown? Are the results for 2 μg/ml LPS-free flu not significant? What do the results lead you to expect in terms of protective effect of vaccine? Why did you not include the positive control (con A)?]

EXAMPLE 10

Liposome-entrapped Plasmid DNA: Characterisation Studies

Materials and Methods

Egg phosphatidylcholine (PC) was purchased from Lipid Products, Nutfield, Surrey, UK. Cholesterol (CHOL), dioleoyl phosphatidylethanolamine (DOPE) and phosphatidylglycerol (PG) were from Sigma, Poole, Dorset, UK and 1,2-dioleoyl-3-(trimethylammonium)propane (DOTAP) from Avanti Polar Lipids, Ala., USA. Polylysine (average molecular weight 22000) was purchased from Sigma, Poole, Dorset, UK. Plasmid pRc/CMV HBS (5.6 kb) expressing the sequence coding for the S region of HBsAg (subtype ayw) was cloned by Dr. R. Shalen using pRc/CMV (Invitrogen) as a vector backbone. The pRc/CMV HBS was radiolabelled with $^{35}$S-dATP by the method of Wheeler and Coutelle and in some experiments, coupled by the same method to the fluorescent marker FluorX dATP from Amersham Life Science, Amersham Place, Buckinghamshire, UK. All other reagents were of analytical grade.

Preparation of Plasmid DNa-containing Liposomes

The dehydration-rehydration procedure was used for the incorporation of pRc/CMV HBS into liposomes. In brief, 2 ml of small unilamellar vesicles (SUV) prepared by sonication and composed of 16 μmol PC, 8 μmol DOPE or CHOL (molar ratio 1:0.5) and 0-16 μmol of the cationic DOTAP or the anionic PG were mixed with 100 μg of plasmid DNA (and $^{35}$S-labelled tracer of the same plasmid) or with 100 μg polylysine (anionic SUV only), frozen at −20° C. and freeze-dried overnight. Controlled rehydration of the dry powders led to the formation of dehydration-rehydration multilamellar vesicles (DRV liposomes). For the preparation of DRV-DNA complexes, DRV prepared as above in the absence of DNA, were incubated at 20° C. for 30 min with 100 μg plasmid DNA mixed with radiolabelled plasmid. DRV preparations were then centrifuged twice at 25000 ×g for 40 min to remove non-entrapped or non-complexed material resuspended in 0.01 M sodium phosphate containing 0.15 M NaCl, pH 7.4 (phosphate-buffered saline, PBS) to the required volume. DNA entrapment into liposomes (DRV(DNA)) or complexation with their surface (DRV-DNA) was estimated on the basis of $^{35}$S radioactivity recovered in the suspended pellets. In some experiments DRV(DNA) or DRV-DNA were made as above in the presence of fluorescent pRc/CMV HBS. In others, cationic SUV (made as above from 0.21 μmol DOPE and 0.21 μmol DOTAP) of similar size (100-150 nm) and identical composition to those of ESCORT Transfection Reagent (DOPE and DOTAP, 1:1 molar ratio; Sigma) were incubated at 20° C. for 30 min with 200 μg of DNA and used as such (SUV-DNA) or freeze-dried to prepare DRV(DNA) as above.

Measurement of Vesicle Size and Zeta-Potential

The z-average diameter of liposomes was measured on an Autosizer 2c by photon correlation spectroscopy (PCS) (DRV or DRV(DNA)) or on a Malvern Mastersizer (DRV-DNA) at 20° C. by diluting 20 μl of the dispersion to the appropriate volume with doubly-filtered (0.22 μm pore size) distilled water. The zeta-potential, which is an indirect measurement of the vesicle surface charge, was measured in 0.001 M PBS at 25° C.

Fluorescence Microscopy

Fluorescence photomicrographs of liposome-entrapped or liposome surface-complexed fluorescent DNA were recorded using a Nikon Microphot FXA using a 340-380 nm wavelength band.

Agarose-gel Electrophoresis

Samples of liposome-entrapped or liposome surface-complexed DNA were subjected to agarose gel (1.0%) electrophoresis to determine the retention of DNA by the liposomes. In brief, 8 μl (1.6-2.0 μg, DNA) of DRV or SUB suspension were mixed with 4 μl gel loading buffer (bromophenol blue 0.05% w/v; sodium dilauryl sulphate, 0.05% w/v; sucrose, 40% w/v; EDTA, 0.1 M; pH 8) and subjected to agarose gel electrophoresis in the presence of ethidium bromide (0.5 μg/ml) for 1 h at 90 V. In some experiments both bromophenol blue and sodium dilauryl sulphate were omitted from the medium. DNA visualisation of the gels was carried out using a UV lamp.

Results and Discussion

Incorporation of DNA Into Liposomes pRc/CMC HBS values of complexation (% of total used) with preformed cationic DRV PC/DOPE liposomes incorporating increasing amounts of DOTAP were 73% (of the total used) for 1 μmol DOTAP but increased to 95-97% ($P<0.05$) for greater amounts of DOTAP (2-16 μmol DOTAP) (Table 9), presumably because DOTAP concentration on the DRV surface was sufficiently high to complex most of the DNA present. In contrast, entrapment of DNA in DRV liposomes was quantitative (94-97%) for all DOTAP contents (Table 9). This could be attributed to the accessibility of much more cationic lipid during the process of dehydration of the cationic SUV-DNA mixture to form, on rehydration, multilamellar vesicles with the DNA mostly distributed in the innter bilayers. It was previously shown that entrapment of the same plasmid DNA (100 μg) in neutral (DOTAP-free) liposomes was significant (48.3%) when the dehydration-rehydration method was employed. On the other hand, when neutral preformed PC/DOPE DRV were incubated with DNA, association with the vesicles (presumably adsorbed to their surface) was low (9.8%). Similar observations were made with anionic PC/DOPE liposomes (Table 10) incorporating increasing amounts of PG (0.5-16 μmol), with DNA entrapment values ranging from 48 to 57%. As expected incubation of preformed anionic DRV (0.5-16 μmol PG) with DNA led to low values (9.2%) of DNA adsorption to the liposomal surface (results now shown).

TABLE 9

Incorporation of DNA into cationic liposomes

| DOTAP content (μmol) | DNA incorporation (% of amount used) DRV-DNA complexes | DRV with entrapped DNA |
| --- | --- | --- |
| 1 | 73.0 ± 14.0 | 95.9 ± 2.5 |
| 2 | 95.0 ± 4.6 | 95.7 ± 2.8 |
| 4 | 96.9 ± 3.7 | 94.0 ± 2.8 |
| 8 | 92.7 ± 6.3 | 96.3 ± 2.0 |
| 12 | 96.0 ± 3.5 | 96.6 ± 3.9 |
| 16 | 97.5 ± 1.2 | 95.5 ± 4.9 |

[35]S-labelled DNA (pRc/CMV HBS; 100 μg) was either complexed (DRV-DNA) with or, entrapped (DRV(DNA)) in liposomes prepared by the dehydration-rehydration procedure and composed of 16 μmol PC, 8 μmol DOPE and 1-16 μmol DOTAP. Values denote mean ± S.D. from five experiments.

Vesicle Size: the Effect of Lipid Components

Figure 10:
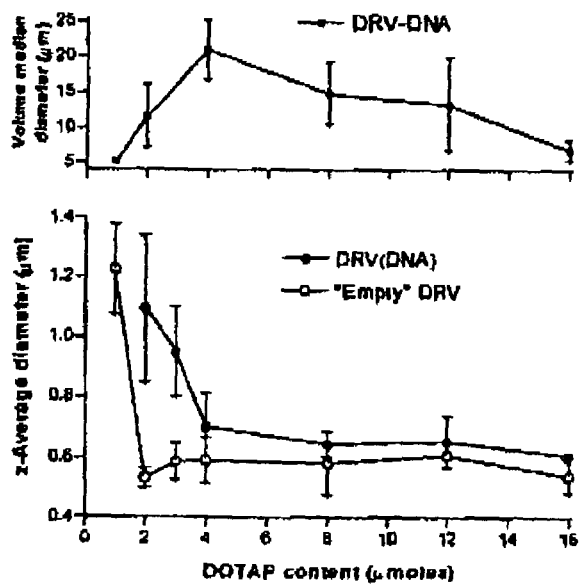

The effect of DOTAP content on the size (diameter) of DRV prepared in the absence or presence of 100 μg DNA is shown in FIG. 10 which shows z-Average diameter of cationic PC/DOPE "empty" DRV and DRV(DNA) prepared in the presence of 100 μg DNA. Vesicle z-average diameter was determined in an Autosizer 2c at 20° C. Values denote means±S.D. (n=4). The size of DRV(DNA) at 1 μmol DOTAP was outside the range of measurement. Differences between DRV(DNA) and empty DRV values were significant for 2 and 3 μmol DOTAP ($P<0.004$). The sizes of DRV-DNA complexes were measured in a Malvern Mastersizer. Results indicate that, at a low DOTAP content (1 μmol), the size of DRV devoid of DNA although considerable (1200 nm), is far lower than that of the same DRV incorporating DNA (DRV(DNA)) where the size is well outside the range of measurement by PCS. However, as the DOTAP content increases, vesicle size is reduced for both preparations, with values becoming similar (580-700 nm) at 4 μmol DOTAP. The same trend of size reduction for both the empty DRV and DRV(DNA) with increasing DOTAP content is also observed (Table 11) when DOPE is replaced by CHOL although vesicle sizes are greater at all DOTAP contents studied (compare Table 11 and FIG. 10). Again, as with the DOPE DRV(DNA) (FIG. 10), CHOL DRV(DNA) vesicles are significantly larger than empty DRV of the same composition (Table 11). The effect of vesicle charge on reducing the size of DRV formed by the method of dehydration-rehydration, could be related to the fusion processes present during the procedure. It is conceivable that charged SUV surfaces repel each other sufficiently so as to interfere with effective membrane fusion, thus leading to smaller DRV. We are not able at present to explain the substantial increase in DRV size when DOPE in the precursor anionic or cationic SUV is replaced by CHOL (table 11). In contrast, the sizes of the complexes formed on mixing preformed cationic DOPE DRV (FIG. 10) or CHOL DRV (legend to Table 11) and 10 μg DNA remained outside the range of measurement by PCS (5-20 μm as measured in the Malvern Mastersizer) regardless of the DOTAP content.

Figure 11:
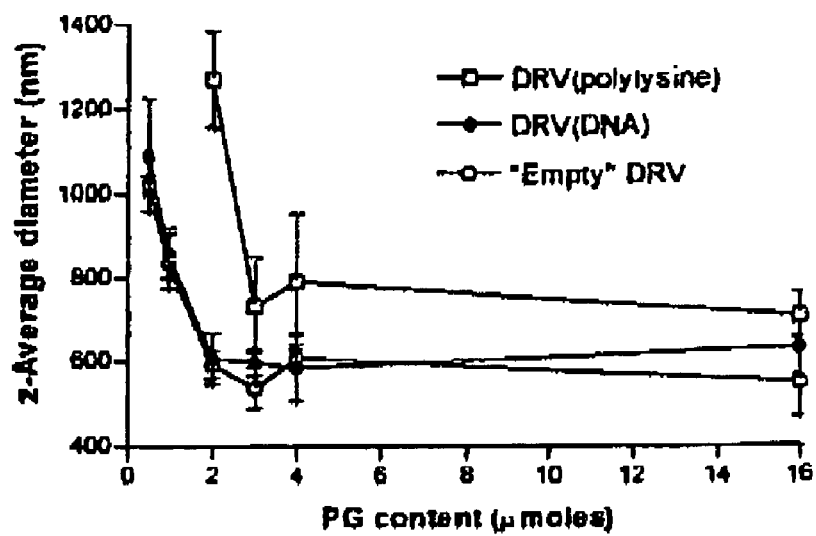

FIG. 11 shows a z-Average diameter of anionic "empty" DRV, DRV(DNA) prepared in the presence of 100 μg DNA, and DRV(polylysine) prepared in the presence of 100 μg polylysine. DRV were composed of 16 μmol PC, 8 μmol DOPE and 0.5-16 μmol PG. Vesicle z-average diameter was determined by PCS at 20° C. Results denote mean±S.D. (n=4).

Similarly to the cationic DRV (FIG. 10) and probably for the same reasons outlined above for cationic DRV, the size of anionic (PG) DNA-free PC/DOPE DRV (FIG. 11) or PC/CHOL DRV (Table 11) is also reduced as the PG content increases. However, in contrast to the cationic DRV, the presence of entrapped DNA does not influence vesicle size (Table 11 and FIG. 11). Moreover, as with cationic DRV, substitution of DOPE with CHOL in anionic DRV results in greater sizes at all PG contents (compare Table 11 and FIG. 11). Interestingly, when the cationic polylysine is entrapped in anionic DRV, the pattern of vesicle size changes with increasing PG content (FIG. 11) is similar to that observed with the cationic DRV entrapping the anionic DNA (FIG. 10): whereas at 1 μmol PG the size of DRV (polylysine) is outside the range of measurement by PCS, size is gradually reduced to become similar to that of empty (anionic) DRV at a PG content above 3 μmol.

Taken together, these results indicate that, within the range of cationic lipid (DOTAP) content (4-16 μmol for 16 μmol PC and 8 μmol DOPE or CHOL) used here, incorporation of 100 μg pRc/CMV HBS into DRV by the dehydration-rehydration procedure leads to the formation of DRV (DNA) constructs that are much smaller (micron or submicron size) than the DRV-DNA complexes seen on mixing the same amount of DNA with preformed DRV of identical lipid composition and concentration. Additional work (results not shown) has revealed that the use of higher amounts of pRC/CMV HBS (e.g. up to 800 μg DNA) for entrapment into PC/DOPE cationic DRV with a low (e.g. 2 μmol) DOTAP content leads to substantial increases in the size (up to 30 μm) of the DRV(DNA) constructs formed. However, this can be avoided by employing a higher DOTAP (e.g. 8 μmol) content whereupon, submicron DRV (DNA) constructs are obtained with a high (>90% of starting material) plasmid content. Assuming an average DNA base residue weight of 320 (and 320 nmol phosphate group charges per 100 μg DNAO, it is of interest that the ratios of positive to negative (+/−) charges used to obtain in the present work the submicron size DRV(DNA) constructs range from 6.25 to 50.00 (for 2 to 16 μmol DOTAP). These +/− values are much higher than those (e.g. 0.08-2.6) used by others in studies with lipoplexes and may explain as to why the latter are often difficult to control in terms of size.

TABLE 10

Incorporation of DNA into anionic liposomes

| PG content (μmol) | DNA incorporation (% of amount used) | |
|---|---|---|
| | PC:DOPE:PG | PC:CHOL:PG |
| 0.5 | 55.0 ± 5.2 | 52.5 ± 3.2 |
| 1 | 53.5 ± 2.7 | 48.3 ± 1.4 |
| 4 | 54.3 ± 9.7 | 47.8 ± 4.4 |
| 16 | 56.8 ± 3.9 | 54.1 ± 5.0 |

$^{35}$S-labelled DNa (pRc/CMV HBS; 100 μg) was entrapped in DRV liposomes composed of 16 μmol PC, 8 μmol DOPE or CHOL and 0.5-16 μmol PG. Values denote mean ± S.D. from at least three experiments.

TABLE 11 z-Average diameter (nm) of CHOL-containing DRV

| DOTAP or PG content | PC:CHOL:DOTAP | | PC:CHOL:PG | |
|---|---|---|---|---|
| (μmol) | DRV | DRV (DNA) | DRV | DRV (DNA) |
| 2 | 1070 ± 122 | outside range | 1181 ± 287 | 1040 ± 277 |
| 4 | 922 ± 90$^a$ | 1290 ± 125$^c$ | 821 ± 136 | 913 ± 70 |
| 8 | 732 ± 123$^b$ | 1154 ± 147$^d$ | 705 ± 40 | 693 ± 28 |

Cationic and anionic "empty" DRV and DRV(DNA) were prepared from 16 μmol PC, 8 μmol CHOL and 2, 4 or 8 μmol of either DOTAP (cationic DRV) or PG (anionic DRV). z-Average diameters were measured using an Autosizer 2c where possible. Results denote mean±S.D. (n=4). Entrapment of DNA, based on $^{35}$S assay of radiolabelled DNA, was 90-95% (cationic) and 50-60% (anionic DRV) of total (100 μg) DNA used. The size of complexes of preformed cationic DRV and DNA as measured in a Malvern Mastersizer were 5-10 μm (results not shown). c vs a, P<0.003 (n=4); d vs b, P<0.005 (n=4). There was no significant difference between sizes of anionic DRV and DRV(DNA) at all PG contents.

Zeta-potential Studies

Values of the zeta-potential of liposomes indirectly reflect vesicle surface net charge and can therefore be used to evaluate the extent of interaction of the liposomal surface cationic charges with the anionic charges of DNA. On this basis, the question of entrapped versus complexed DNA in the PC/DOPE DRV(DNA) cationic liposomes was investigated using DRV with entrapped DNA and preformed DRV before and after complexing with DNA.

Figure 12:
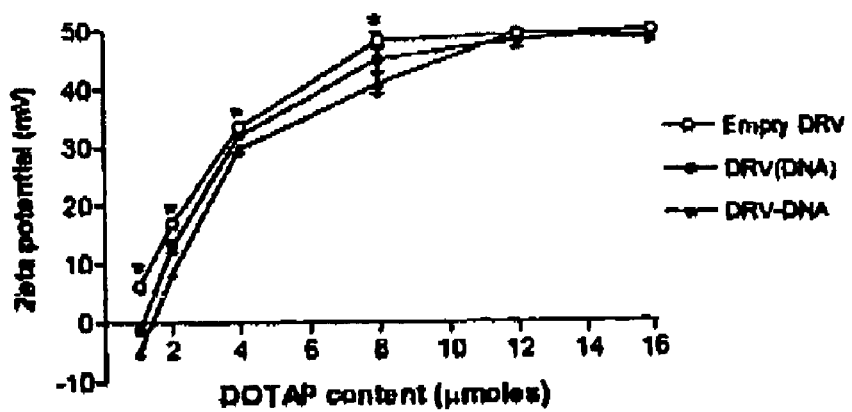

FIG. 12 shows Zeta-potential of DRV liposomes. "Empty" DRV, DRV-DNA and DRV(DNA) composed of 16 μmol PC, 8 μmol DOPE and 1-16 μmol DOTAP were prepared in the presence of 100 μg DNA where appropriate and subjected to microelectrophoresis. Values denote mean±S.D. from five measurements. *Indicates statistically significant (P<0.03–0.0001) differences in values between empty DRV and DRV(DNA) or DRV-DNA. Differences between DRV(DNA) and DRV-DNA were significant as follows for the μmol of DOTAP shown in parentheses; P<0.001 (1), P<0.01 (2), P<0.035 (4) and P<0.032 (8).

Results in FIG. 12 show trends of increasing zeta-potential values with increasing DOTAP content (1-16 μmol) for all preparations, with absolute values (for up to 8 μmol DOTAP) being in the order of "empty" DRV>DRV(DNA) >DRV-DNA. As similar amounts of DNA were present in DRV(DNA) (94-96 µg) and DRV-DNA (73-96 µg), results suggest that in the latter case there is more DNA on the vesicle surface (thus neutralising more of the cationic charges) and that, with DRV(DNA), some of the DNA is located within the liposomes, presumably bound to cationic charges hidden in the inner bilayers. However, with DOTAP content at 12 µmol or more (FIG. 12), the amount of DNA present in DRV(DNA) and DRV-DNA is probably too low (relative to DOTAP) to cause measurable differences in their zeta-potential values.

Figure 13:
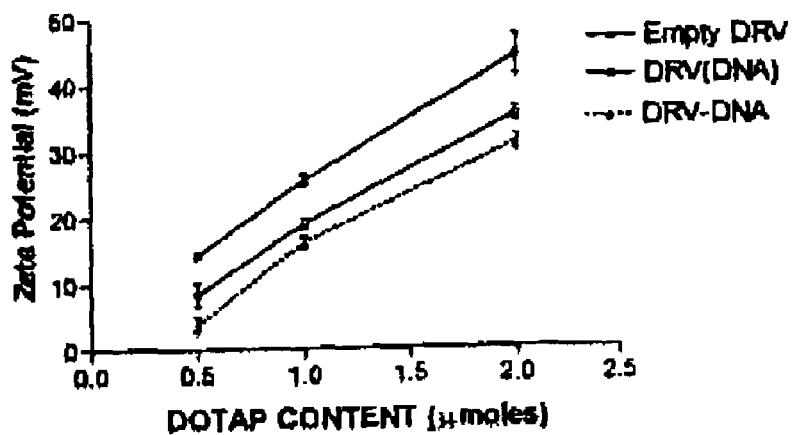

FIG. 13 shows the Zeta-potential of DRV liposomes. "Empty" DRV, DRV-DNA and DRV(DNA) composed of 16 µmol PC, 8 µmol CHOL and 0.5-2 µmol DOTAP were prepared in the presence of 100 µg DNA where appropriate and subejcted to microelectrphoresis. Results denote mean±S.D. from five measurements. The same order of zeta-potential values (i.e. empty DRV>DRV(DNA)>DRV-DNA) was observed when DOPE in PC/DOPE DRV was replaced with CHOL, although values in this case were much greater (FIG. 13; 0.5-2 µmol DOTAP) than those seen when DOPE was present (FIG. 11; 1-2 µmol DOTAP). This could be attributed either to the zwitterionic nature of DOPE (at pH 7.4) which, when present, would lead to the masking of some of the cationic charges of DOTAP or to CHOL in some way rendering such charges more available for measurement, or both. As with the PC/DOPE DRV, there was no difference in the zeta-potential values for the CHOL-containing PC DRV(DNA) and DRV-DNA when the DOTAP content increased above a certain level (e.g. 51.6±1.0 mV for 4 µmol DOTAP content with both formulations; results not shown).

Figure 14:
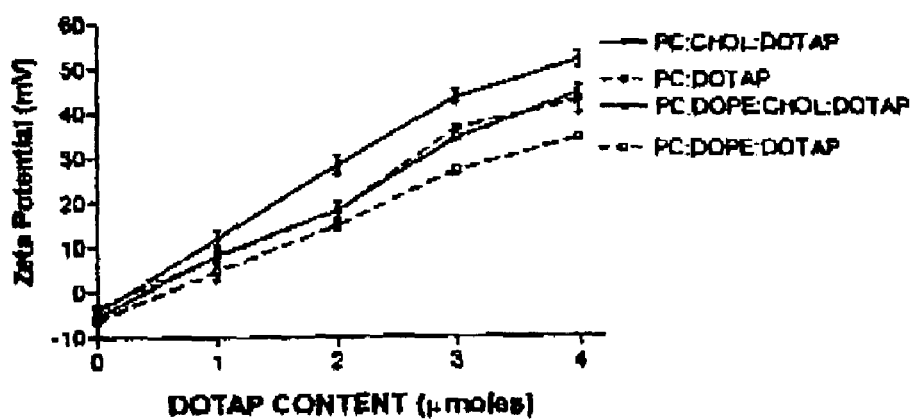
Figure 15:
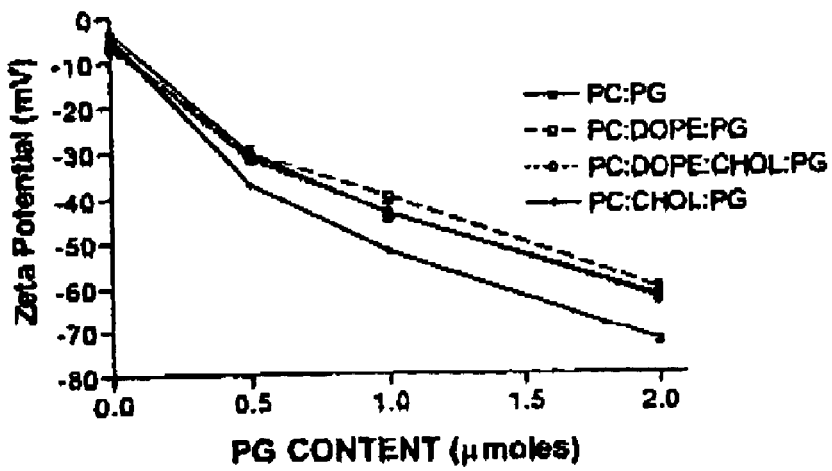
Figure 16:
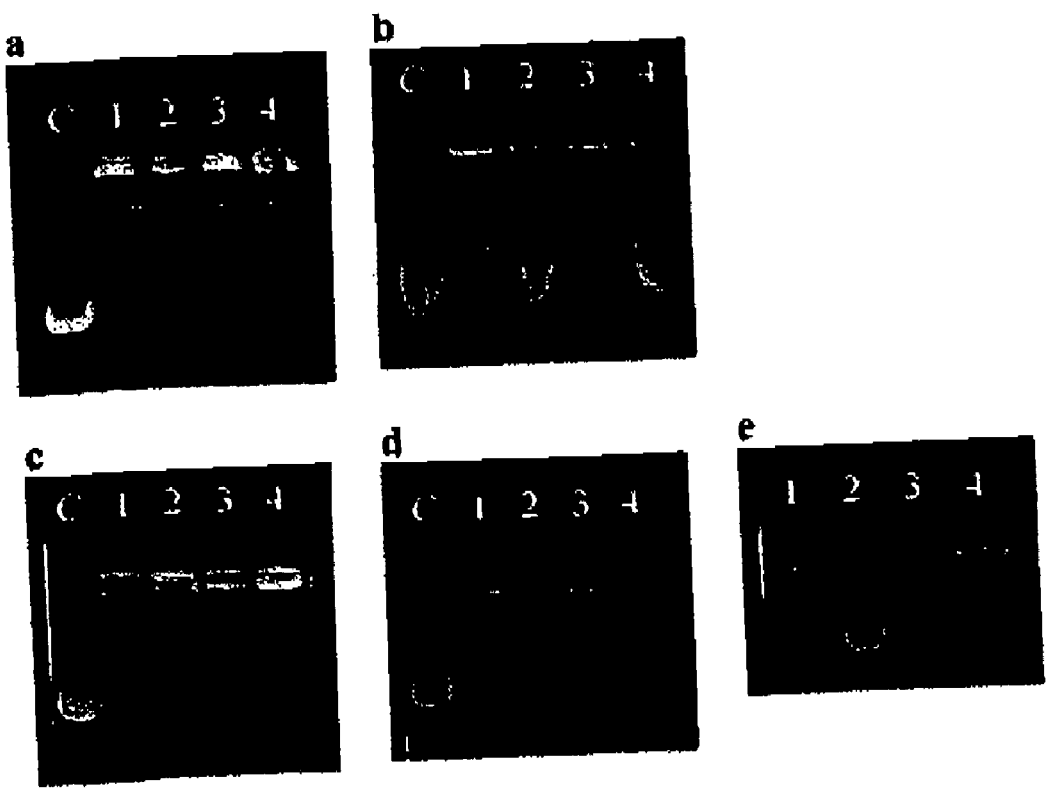

FIG. 14 shows the role of the zwitterionic DOPE and of CHOL on the zeta-potential values was further clarified in experiments (FIG. 14) where DNA-free cationic PC DRV as such (PC/DOTAP) or supplemented with DOPE, CHOL or both lipids, were measured for zeta-potential values. Results clearly show that for all DOTAP contents (1-4 µmol) studied, values are decreased or increased by the presence of DOPE and CHOL, respectively, whereas in the presence of both lipids values remain unaltered (i.e. similar to those of PC/DOTAP DRV), probably because the two lipids cancel each other (FIG. 14). FIG. 15 shows Zeta-potential of "empty" DRV liposomes composed of 0-2 µmol PG and 24 µmol PC (PC:PG), 16 µmol PC and 8 µmol DOPE (PC:DOPE:PG), 16 µmol PC, 4 µmol DOPE and 4 µmol CHOL (PC:DOPE:-CHOL:PG). All four preparations exhibited similar zeta-potential values (−3.5 to −6.3 mV) in the absence of PG. Results denote mean±S.D. from five measurements.

The effect of CHOL on the net charge of the liposomal surface was also observed with DNA-free DRV preparations in which DOTAP was substituted with the anionic PG (FIG. 15): addition of CHOL to DRV led to greater availability of the ionic charges and reduction of the zeta-potential values for all PG contents studied. Again, there was no change when both CHOL and DOPE were present.

Fluorescence Microscopy Studies

The results on DNA incorporation with the neutral (see above) and anionic (Table 11) PC/DOPE DRV strongly suggest that most of the pRc/CMV HBS plasmid is entrapped within the aqueous spaces of the multilamellar vesicles rather than being absorbed to their surface. In the case of cationic PC/DOPE DRV, however, because of the similarity of DNA association values for the DRV(DNA) and the DRV-DNA preparation (Table 9), actual DNA entrapment within the vesicles (as opposed to surface complexation) cannot be ascertained. On the other hand, the observed submicron vesicle size of DRV(DNA) with increased DOTAP content (>4 µmol) as opposed to the much larger size of DRV-DNA complexes under the same conditions (FIG. 10), as well as differences in zeta-potential values (FIGS. 13 and 14) are indicative of differences in the mode of DNA interaction with the cationic charges of the two constructs. This was further substantiated when liposomes with "entrapped" or complexed fluorescent DNA were examined under fluorescence microscopy: in contrast to the relatively small fluorescent particles observed in the case of DRV(DNA), DRV-DNA complexes were seen as large aggregates of various sizes. Similarly large aggregates mixed with smaller aggregates were also observed with the SUV-DNA complexes used for the preparation of DRV (DNA), strongly suggesting a re-organisation of these complexes during the dehydration-rehydration procedure to product discrete DRV(DNA) vesicles constructs rather than the DRV-DNA complexes.

The spatial localisation of DNA within the cationic DRV (DNA) and DRV-DNA preparations was also investigated by subjecting these to gel electrophoresis in the presence of sodium dilauryl sulphate (SDS) at a concentration (0.05%) below the critical micelle concentration of the surfactant. It was anticipated that the anionic SDS, although unable to solubilise the liposomal lipids, would be able to partition into the outer monolayer of the constructs, compete with DNA bound to the cationic surface charges and release it into the medium. Released DNA would then be expected to migrate towards the cathode, with DNA unavailable (presumably entrapped) to SDS remaining at the site of application.

FIGS. 16*a-e* show the following results:

Gel electrophoresis of DRV(DNA) (lanes 1 and 3) and DRV-DNA (lanes 2 and 4) composed of 16 µmol PC, 8 µmol DOPE and 1 (lanes 1 and 2) or 2 µmol (lanes 3 and 4) DOTAP. Lane C, naked DNA. (b) As in (a) but in the presence of the anionic SDS. (c) Gel electrophoresis of DRV(DNA) (lanes 1 and 3) and SUV-DNA (lanes 2 and 4) both composed of 16 µmol PC, 8 µmol DOPE and 1 (lanes 1 and 2) or 2 µmol (lanes 3 and 4) DOTAP. Lane C, naked DNA. (d) As in (c) but in the presence of the anionic SDS. (e) Gel electrophoresis of DRV(DNA) (lane 1) composed of 0.21 µmol DOPE and 0.21 µmol DOTAP and the precursor SUV-DNA (lane 2) (used to prepare the DRV(DNA) of lane 1; see Section 2). Lanes 1 and 2: SDS present; lanes 3 and 4: no SDS.

FIG. 16*a* shows that, on gel electrophoresis of PC/DOPE DRV(DNA) and DRV-DNA in the absence of anionic molecules, DNA remains at the site of application, bound to cationic charges of the preparations. In contrast, following electrophoresis in the presence of SDS (FIG. 16*b*) displaced DNA is seen to migrate towards the cathode. As expected, much more DNA is displaced in the DRV-DNA complexes (FIG. 16*b*, lanes 2 and 4) than the DRV with the entrapped DNA (lanes 1 and 3). DNA displacement in the presence of SDS was also shown to occur in DNA complexes with the cationic PC/DOPE SUV (FIG. 16*d*, lanes 2 and 4) used as precursors for the generation of the multilamellar cationic DRV as well as DNA complexes with the ESCORT Transfection Reagent type DOPE/DOTAP SUV (FIG. 16*a*, lane 2) but not in its absence (FIG. 16*c*, lanes 2 and 4, and *e*, lane 4, respectively). Again, there was much less DNA displacement with DRV made from such (precursor) vesicles (FIG. 16*d*, lanes 1 and 3, and *e*, lane 1, respectively). It has been suggested that cationic DOPE SUV (such as the ESCORT Tranfection Reagent vesicles used here) incubated with appropriate amounts of plasmid DNA to give cationic lipid/

DNA charge ratios that are similar to those in the present work, form larger complexes (lipoplexes) in which DNA is localised within bilayers, bound electrostatically to the cationic charges. However, the observation (FIG. 16d, lanes 2 and 4 and e, lane 2) that such lipoplexes lose most of their DNA content on electrophoresis in the presence of SDS, indicates that the structural characteristics of lipoplexes are such that SDS is allowed to access DNA and displace most of it. As this does not occur with ESCROT vesicle-derived DOPE DRV(DNA) (FIG. 16e, lane 1) or with PC/DOPE SUV-derived DRV(DNA) (FIG. 16d, lanes 1 and 3), such DRV are likely to incorpoate most of their DNA within closed bilayers, probably bound to the inner cationic charges.

In conclusion, several lines of evidence including vesicle size and vesicle surface zeta-potential measurements, morphological observations (fluorescent microscopy) and anion competition experiments (gel electrophoresis), strongly suggest that the localisation of plasmid DNA in the cationic multilamellar DRV liposomes produced by the dehydration-rehydration procedure is different not only from that obtained on DNA complexation with preformed cationic DRV but also from SUV-DNA complexes that are used as precursors for the production of cationic DRV. It appears that freeze-drying of these large SUV-DNA complexes (or lipoplexes) and subsequent rehydration results in smaller structures where DNA is predominantly entrapped within the bilayers, presumably bound to the inner cationic charges. Some of the DNA also interacts with surface charges and it is probably this minor portion of DNA that is displaced by SDS on gel electrophoresis (e.g. FIG. 16, lane 1). In contrast, a much greater quantity of DNA is displaced in the DRV-DNA (FIG. 16b, lanes 2 and 4) or SUV-DNA (e.g. FIG. 16d, lanes 2 and 4, and e, lane 2) complexes, an event that indicates predominant DNA binding to external surfaces.

EXAMPLE 11

Liposome-mediated DNA Vaccination: the Effect of Vesicle Composition

Materials and Methods

Materials

The sources and grades of egg phosphatidylcholine (PC), phosphtidylethanolamine (PE), dioleoyl phosphatidylethanolamine (DOPE), cholesterol (CHOL) and 1,2-dioleoyl-3-(trimethylammonium)propane (DOTAP) have been described above. Plasmid pRc/CMV HBS (5.6 kb) expressing the sequence coding for the S (small) region of HBsAg (subtype ayw) was supplied by Aldevron (Fargo, N. Dak., USA) and pCMV.EGFP encoding enhanced green fluorescent protein was a gift from Dr Steven Hart. Both plasmids were radiolabelled with $^{35}S$ as described elsewhere [15, 19]. Horseradish peroxidase-conjugated goat anti-mouse immunoglobulin $IgG_1$, $IgG_{2a}$ and $IgG_{2b}$, and foetal calf serum were obtained from Sera-Lab (Crawley Down, Sussex, UK). Ninety-six-well flat-bottomed microtitre plates (Immunolon IB) were purchased from Dynatech Labs (Billingshurst, Sussex, UK). Recombinant hepatitis B surface antigen (HBsAg) (S region; ayw subtype) was supplied by Genzyme diagnostics (Kingshill, Kent, UK). All other reagents were of analytical grade.

Preparation of Plasmid DNA-containing Liposomes pRc/CMV HBS was incorporated into liposomes by the dehydration-rehydration procedure. In brief, 2 ml small unilamellar vesicles (SUV) prepared by sonication and composed of 16 μmol PC or DSPC, 8 μmol DOPE, PE or cholesterol (molar ratio 1:0.5) and 1-16 μmol cationic lipid DOTAP were mixed with 100 μg plasmid DNA (and $^{35}S$-labelled tracer of the same plasmid) to form lipoplexes, frozen at -20° C. and freeze-dried overnight. Controlled [15-19] rehydration of the dry powders led to the formation of multilamellar dehydration-rehydration vesicles (DRV liposomes) containing the DNA within their structure, presumably bound to the cationic charges of the inner bilayers DNA-containing DRV (DRV(DNA)) were then centrifuged twice at 25000 g for 40 min to remove non-entrapped DNA and resuspended in 0.01 M sodium phosphate containing 0.15 M NaCl (pH 7.4) (phosphate-buffered saline (PBS)) to the required volume. DNA entrapment into liposomes (Tables 12 and 13) was estimated on the basis of $^{35}S$ radioactivity recovered in the suspended pellets. The same procedure as already described was used to entrap pCMV.EGFP (100 μg) into DRV composed of 16 μmol PC, 8 μmol DOPE and 4 μmol DOTAP.

Determination of Vesicle Size

The z-average diameter of DRV(DNA) liposomes was measured on a Autosizer 2c by photon correlation spectroscopy (PCS), at 20° C. by diluting 20 μl dispersion to the appropriate volume with doubly filtered (0.22 μm pore size) distilled water.

Determination of Vesicle Zeta Potential

The zeta potential, an indirect measurement of the vesicle surface charge, was measured in 0.001 M PBS at 25° C. on a Malvern Zetasizer 3000.

Electron Microscopy

Cryo-electron microscopy of DRV(DNA) involved [24] forming a thin aqueous film on bare specimen grid (3-4 μm thick, with a fine 700 mesh honeycomb pattern of bars) by dipping the grid into the liposome suspension. After blotting the suspension-coated grid on filter paper, the thin film produced was rapidly (1 s) vitrified by plunging the grid into ethane and cooled to its melting point with liquid nitrogen. Preparation and blotting of thin films was carried out in a controlled environment using a fully automated system (PC-controlled, up to vitrification). The vitrified film was mounted in a cryo-holder (Gatan 626) and observed at -170° C. in a transmission microscope (Philips CM12) operating at 120 kV. Micrographs were taken using low-dose conditions.

Immunisation Protocol

Female Balb/c mice, 6-8 weeks old, were given two to four intramuscular (hind leg) injections of 10 μg (in 0.1 ml PBS) of either "naked" or liposome-entrapped pRcoCMV HBS plasmid as described further below. Sera samples collected at time intervals were tested for anti-HBsAg (S region; ayw subtype) $IgG_1$, $IgG_{2a}$ and $IgG_{2b}$ by the enzyme-linked immunoadsorbent assay (ELISA) as previously described. Engogenous levels of interferon-γ (IFN-γ) and interleukin-4 (IL-4) in whole spleens were determined by the method of Nakane et al as modified by de Souza et al. Individual spleens from mice injected intramuscularly twice with 10 μg naked or liposome-entrapped pRc/CMV HBS and with 1 μg HBsAg (in 0.2 ml of 0.9% NaCl) intravenously 24 h before death, were weighed, homogenised in ice-cold RPMI containing 1% 3-(cholamidopropyl-o-dimethylammonio)-1-propane-sulphonate (CHAPS; Sigma) in a Dounce tissue homogeniser and 10% (w/v) homogenates were prepared. Homogenates were left on ice for 1 h and insoluble debris was removed by centrifugation at 2000 g for 20 min. Standard capture ELISAs were used to determine IFN-γ and IL-4 levels. Maxisorb (NUNC, UK) plates were coated with primary monoclonal antibodies against IFN-γ and IL-4. Secondary biotinylated antimouse IL-4 and antimouse IFN-γ monoclonal antibodies (Pharmingen, USA) were used with streptavidin peroxidase (Dako, Denmark) and o-phenylenediamine (Sigma) as substrate. Recombinant IFN-γ and IL-4 standards were from Pharmingen. Spleens from a group of non-immunised (intact) mice treated as already described served as controls. Results (mean±S.D.) expressed as nanograms per spleen from at least four mice were analysed and compared using the Student's t-test.

Expression of Enhanced Green Fluorescent Protein After Intramuscular Injection of the Plasmid Encoding the Protein Female Balb/c mice, 6-8 weeks old, in groups of three were injected intramuscularly into the right hind leg with 10 µg (in 0.1 ml PBS) of naked or liposome-entrapped PCM-V.EGFP. Forty-eight hours later, muscle tissue from the injected sites and the popliteal and inguinal lymph nodes were collected, adhered to crystat chucks using Tisue-Teck (Miles Inc., USA) and frozen in liquid nitrogen, and sections (20 µm) cut in a Slee cryostat. Images were captured in a Nikon microphot-fxa microscope using incident fluorescence and Kodak ektachrome 400 ASA film.

for pCMV.EGFP (footnote to Table 12), have been found to be reliable and to predominantly reflect actual DNA entrapment as opposed to vesicle surface complexation. The latter occurs when preformed "empty" (water-containing) cationic liposomes are incubated with DNA resulting in aggregates of 10-20 µm diameter. In contrast, DRV(DNA) are much smaller (around 1 µm diameter) (Table 12) and appear to contain the DNA within the aqueous spaces in between the bilayers, presumably bound to the cationic charges. Indeed, cryo-electron microscopy of DRV(DNA) clearly showed that such constructs are multilamellar vesicles of similar appearance to that already seen by cryo-electron microscopy of neutral DRV-containing anions. The multilamellar structure of DRV(DNA) was further confirmed (results not shown by freeze fracture electron microscopy as previously applied for neutral DRV.

Table 12 (and footnote for pCMV.EGFP) also shows zeta potential values for DRV(DNA). Judging from results with pRc/CMV HBS, such values are influenced by the presence of DOPE or PE. Thus, values are lower (31-33 mV) when

TABLE 12

Incorporation of plasmid DNA into liposomes: entrapment, zeta potential, and vesicle size

| Liposomes | DNA incorporation (% of used) | Zeta potential (mV) | Size (nm ± S.D. (PDI)) |
|---|---|---|---|
| PC:DOPE:DOTAP (16 µmol:8 µmol:4 µmol) | 94.0 ± 2.8 | 32.1 ± 0.3 | 979.3 ± 95.9 (0.32) |
| PC:PE:DOTAP (16 µmol:8 µmol:4 µmol) | 92.3 ± 4.1 | 32.9 ± 0.7 | 1093.6 ± 81.3 (0.39) |
| DSPC:DOPE:DOTAP (16 µmol:8 µmol:4 µmol) | 91.3 ± 3.3 | 32.6 ± 0.4 | 1024.6 ± 152.6 (0.30) |
| PC:CHOL:DOTAP (16 µmol:8 µmol:4 µmol) | 87.9 ± 3.9 | 53.9 ± 1.5 | 934.6 ± 138.3 (0.35) |
| PC:DOTAP (16 µmol:8 µmol:4 µmol) | 90.0 ± 4.6 | 43.0 ± 3.0 | 976.2 ± 87.2 (0.31) |

[a] $^{35}$S-labelled pRc/CMV HBS (100 µg) was incorporated into cationic DRV of various lipid compositions and lipid molar ratios as shown. Incorporation values were based on $^{35}$S assay. The zeta potential of the DRV was measured in 0.001 M PBS at 25° C. using a Zetasizer 3000. Vesicle z-average diameter was determined in an Autosizer 2c at 20° C. Results represent mean ± S.D., n = 3-5. Corresponding values for pCMV.EFGP (100 µg) entrapped in PC:DOPE:DOTAP (16:8:4 molar ratios) liposomes were 94 ± 4.0 (% entrapped), 32.3 ± 0.4 (mV) and 689 ± 88 (nm ± S.D.) n = 3).

TABLE 13

The effect of DOTAP content of DRV on DNA incorporation, vesicle size and zetal potential

| DOTAP content (µmol) | Incorporation (% used) | Zeta potential (mV) | Vesicle size (nm) |
|---|---|---|---|
| 1 | 95.9 ± 0.5 | −1.1 ± 0.8 | n/d |
| 2 | 95.7 ± 2.8 | 13.2 ± 1.1 | 1095 ± 247 |
| 4 | 94.0 ± 2.8 | 32.1 ± 0.3 | 703 ± 109 |
| 8 | 96.3 ± 0.9 | 45.0 ± 2.3 | 645 ± 62 |
| 12 | 96.6 ± 2.8 | 48.3 ± 1.5 | 653 ± 84 |
| 16 | 95.5 ± 4.9 | 49.7 ± 0.2 | 607 ± 97 |

[a] $^{35}$S-labelled pRc/CMV HBS (100 µg) as in Table 1 was incorporated into DRV composed of 16 µmol PC, 8 µmol DOPE and various amounts of the cationic lipid DOTAP. Vesicle size (z average diameter) for DRV(DNA) containing 1 µmol DOTAP was too great to be measured by PCS and hence no determined (n/d). For other details, see footnote to Table 1. Results represent mean ± S.D., n = 3-5.

Results and Discussion

DNA Incorporation Into Liposomes

Values of pRc/CMV HBS entrapment (% of total used) in DRV of all compositions studied (Tables 12 and 13) were high (88-97%), even when the amount of cationic lipid (DOTAP) employed per preparation was as low as 1 µmol (Table 13). The use of DSPC (a high gel to liquid crystalline transition temperature ($T_c$) lipid) instead of PC or substitution of DOPE with PE had no influence on DNA entrapment values. Such $^{35}$S-based entrapment values, also confirmed these lipids are present than when omitted (e.g. 43 mV for PC:DOTAP; Table 12) or substituted with cholesterol (e.g. 54 mV for PC:CHOL:DOTAP; Table 12). Interestingly, DOPE was found to also reduce the negative z-potential of similar phosphatidyl glycerol-incorporating anionic liposomes when compared with anionic vesicles where cholesterol replaces DOPE. It has been suggested that such reductions of z-potential to less positive or less negative values in the presence of DOPE or PE result from the formation of salt bridges between the charge-bearing head groups of DOTAP or phosphatidyl glycerol and the zwitterionic head group of phosphatidylethanolamines. There was no significant difference in the zeta potential values between DSPC and PC DRV(DNA) (Table 12). As expected, and already found for a variety of polymer-DNA complexes, increasing the cationic lipid content of DRV(DNA) (incorporating a constant amount of DNA) led to an increase (from about 1 to 50 mV) in zeta potential values (Table 13).

The effect of DOTAP content on the size (diameter) of DRV prepared in the presence of 100 µg DNA is shown in Table 13. Results indicate that, as the DOTAP content increases to 2 µmol or higher, vesicle size is reduced to around 600-1100 nm (see also footnote to Table 12 for liposome-entrapped pCMV-EGFP). This effect of vesicle charge on the size reduction of DRV(DNA) has been attributed (in Example 10) to the charged surfaces repelling each other sufficiently during the dehydration rehydration steps of the DRV procedure so as to interfere with the progress of membrane adhesion and eventually fusion, thus leading to smaller DRV.

Immunisation with Liposome-entrapped DNA

Having already established that intramuscular injection of DRV(DNA) is more effective in inducing immune responses to the encoded antigen than injection of naked DNA or DNA complexed with preformed DRV, further related work was carried out to study the effect of varying the lipid composition of liposomes as well as their cationic charge on such responses. To allow the detection of liposome-mediated improvement (if any) of immune responses to the encoded antigen, doses of plasmid DNA were, as previously in Examples, low enough (10 µg) for naked DNA to fail to induce responses under the present conditions. In this respect, other workers using the same (naked) pRc/CMV HBS plasmid employed multiple doses of 50-100 µg in order to obtain substantial levels of anti-HBsAg IgG.

Figure 17:
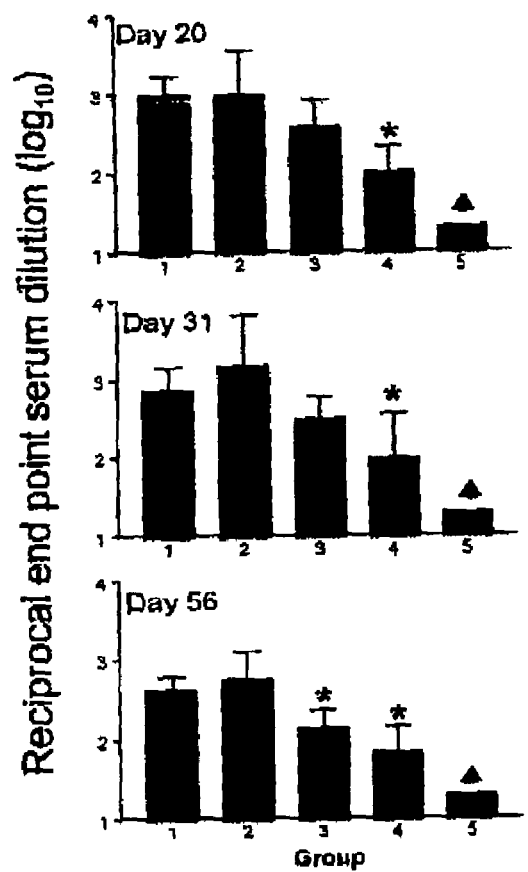

FIG. 17 shows results for immunisation with liposome-entrapped PRCMV HBS: the effect of lipid composition. Balb/c mice in groups of five were injected intramuscularly on days 0, 14 and 35 either with 10 µg naked DNA (group 5) or with 10 µg pRc/CMV HBS entrapped in cationic liposomes composed of PC, DOPE and DOTAP (4:2:1 molar ratio, group 1); PC'PE and DOTAP (4:2:1 molar ratio, group 2); PC; CHOL and DOTAP (4:2:1 molar ratio, group 3); PC and DOTAP (4:1 molar ratio, group 4). Values at days 55, 66 and 91 after the first injection are means±S.D. (n=5) of $\log_{10}$ of the reciprocal end-point serial twofold serum dilutions required for OD readings to reach a value of about 0.200. Sera from untreated mice gave $\log_{10}$ values of less than 2.0.* Values significantly (P<0.01–0.001) lower than those of the groups 1 and 2; ▲, values significantly (P<0.03–0.0001) lower than those of groups 1-4.

FIG. 17 shows $IgG_1$ responses in mice 55, 66 and 91 days after the first of three injections of 10 µg pRc/CMV HBS, either naked or entrapped in liposomes composed of lipids as shown in Table 12 (the figures indicate the days after the third injection). Results reveal that, at all time points measured, mice immunised with DRV(DNA) (FIG. 17, groups 1-4) elicited significantly higher (P>0.03–0.0001) immune responses than mice injected with naked DNA (FIG. 17, group 5). Moreover, there was no significant difference in responses when DOPE in DRV(DNA) was replaced by PE (FIG. 17, compare groups 1 and 2). However, responses were significantly (P<0.01–0.001) reduced when the DOPE component in DRV(DNA) was omitted (FIG. 17, compare groups 1 and 4). A significant (P<0.01–0.001) reduction in $IgG_1$ response was also observed when DOPE in DRV (DNA) was replaced by cholesterol (FIG. 17, compare groups 1 and 3; 91 days). Incorporation of DOPE into the vesicle bilayer is known to enhance the transfection activity in vitro of liposome-DNA complexes (lipoplexes), possibly because of the ability of DOPE to enter the $H_{II}$ hexagonal phase. It is thought that, by entering the $H_{II}$ phase after the endocytosis of lipoplexes, DOPE promotes the disruption of the endosomal membrane and ensuing escape of plasmid DNA into the cytoplasm. The data of FIG. 16 indicating greater immune responses for DRV(DNA) incorporating DOPE (or PE), support this view: increased concentration of the plasmid in the cytoplasm as a result of the membrane disrupting activity of phosphatidylethanolamine should lead to a greater probability of plasmid entry into the nucleus and subsequent expression.

Figure 18:
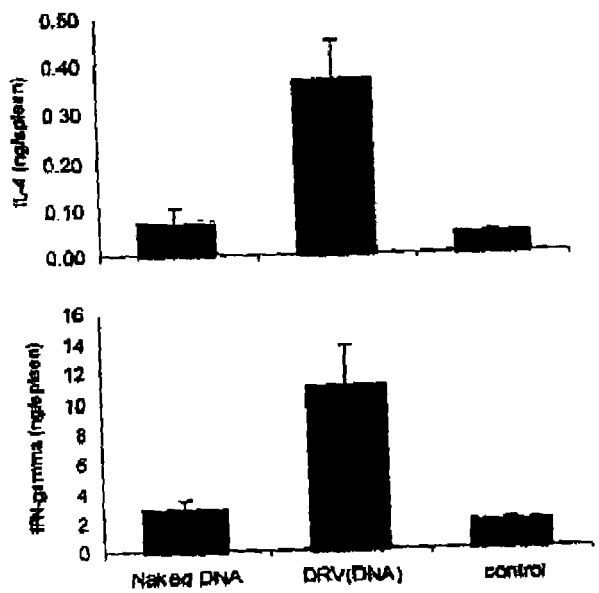

In a separate experiment using pRc/CMV HBS (10 µg), either as such (naked) or entrapped in DRV composed of PC, DOPE and DOTAP, cell-mediated immunity was measured in terms of endogenous IFN-γ content of the spleens of mice immunised with pRc/CMV HBS and injected intravenously with 1 µg encoded antigen 24 h before death. FIG. 18 shows the results for Interferon-γ and interleukin IL-4 levels in the spleens of mice immunised with naked or liposome-entrapped pRCMV HBS Balb/c mice in groups of four were injected on days 0 and 21 with 10 µg pRc/CMV HBS either in the naked form or entrapped in liposomes composed of 16 µmol PC, 8 µmol DOPE and 4 µmol DOTAP (DRV(DNA)). "Control" represents cytokine levels in normal, non-immunised mice. Forty-one days after the first injection, mice were injected intravenously with 1 µg HBsAg, killed 24 h later and their spleens subjected to cytokine analysis as described above. Each bar represents the mean±S.D. of a group of four mice indicate much greater levels of the cytokine in the spleen of mice immunised with the liposome-entrapped plasmid. The failure to detect significant levels of IFN-γ in the present study in animals injected with naked plasmid could be attributed to the low amount used (10 µg). Levels of IL-4 representing humoural immunity were also higher in the animals treated with liposomal plasmid, confirming data in FIG. 17.

Figure 19:
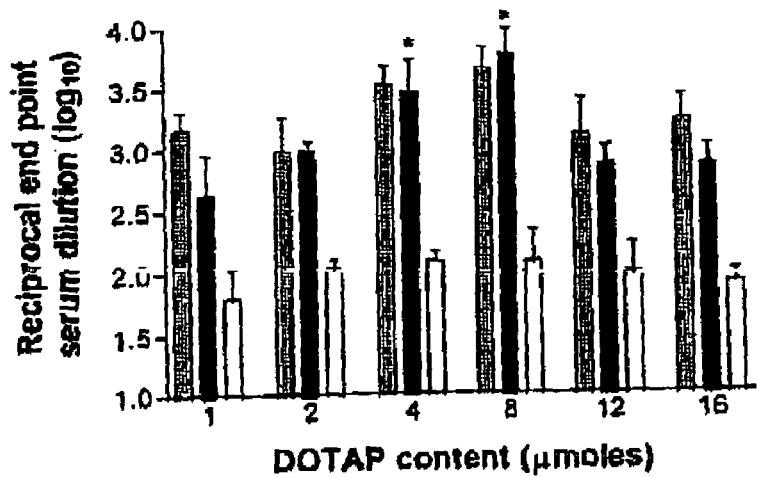
Figure 20:
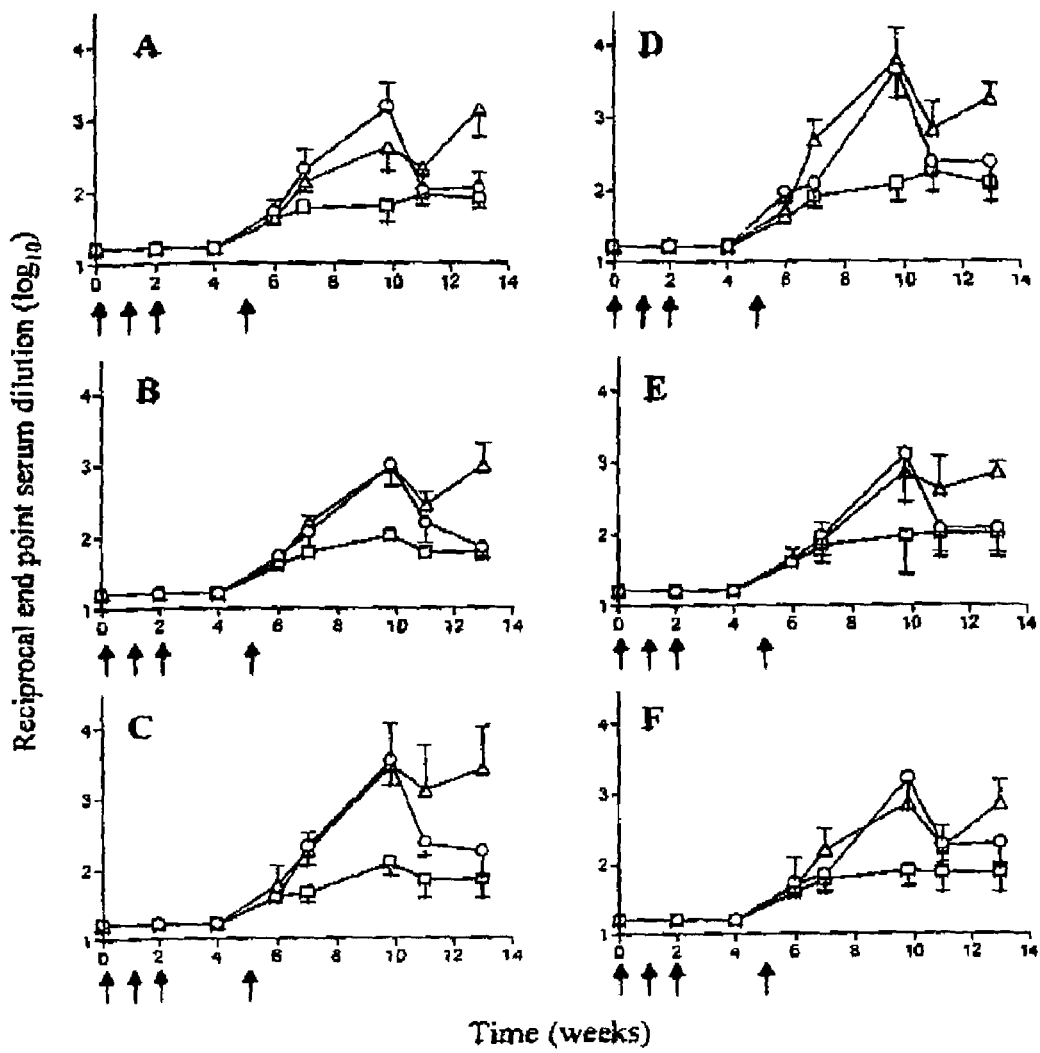

In another experiment, the effect of cationic change was investigated. FIG. 19 shows the results for immunisation with liposome-entrapped pRCMV HBS: the effect of cationic charge. Balb/c mice in groups of five were injected intramuscularly on days 0,7,14 and 35 with 10 µg pRc/CMV HBS entrapped in cationic liposomes composed of 16 µmol PC, 8 µmol DOPE and 1-16 µmol DOTAP. Sera samples at 69 days after the first injection were tested by ELISA for $IgG_1$ (dotted bars), $IgG_{2a}$ (black bars) and $IgG_{2b}$ (open bars) responses against the encoded hepatitis B surface antigen. For other details see description of FIG. 17.* $IgG_{2a}$ responses significantly higher (P<0.02–0.006) than those in mice immunised with other DOTAP formulations. IgG responses were monitored in mice immunised with pRc/CMV HBS entrapped in DRV composed of PC and DOPE but incorporating a wide range of DOTAP content (1-16 µmol). Results in FIG. 19 showing maximum IgG subclass ($IgG_1$, $IgG_{2a}$ and $IgG_{2b}$) levels attained 69 days after the first injection suggest a trend of higher responses when 4 or 8 µmol DOTAP are present in the DRV(DNA). For instance, $IgG_{2a}$ values from mice immunised with these formulations were significantly higher (P<0.02–0.006) than those from mice immunised with other DRV(DNA) preparations incorporating lower or higher amounts of DOTAP. There was no significant difference in $IgG_{2b}$ responses with any of the groups. These results suggest that the presence of 4 or 8 µmol DOTAP in DRV (which relates to a theoretical +/− charge ratio of 3.2:1 to 6.4:1) may be an optimum cationic lipid to DNA ratio to employ in liposome-mediated vaccination. However, even with small amounts of cationic lipid (1 μmol) present, significant immune responses can be obtained and this may be of importance if higher amounts of cationic lipid prove to be toxic. The courses of IgG responses are shown in FIG. 20 i.e. for immune responses in mice immunised with liposome-entrapped pRCMV HBS in the experiment of FIG. 18 Sera samples were collected at various time intervals and tested by ELISA for $IgG_1$ (circles), $IgG_{2a}$ (triangles) and $IgG_{2b}$ (squares) responses against the encoded hepatitis B surface antigen. (A) 1 μmol DOTAP, (B) 2 μmol DOTAP, (C) 4 μmol DOTAP, (D) 8 μmol DOTAP, (E) 12 μmol DOTAP, and (F) 16 μmol DOTAP. For other details, see description of FIG. 19.

Inspection of the time course of IgG subclass values (FIG. 20) revealed no responses until week 6, after which values (especially for $IgG_1$ and $IgG_{2a}$) increased to peak at week 10 for all DOTAP contents. By week 13, all DOTAP groups showed a fall in $IgG_1$ responses whereas, in most cases, $IgG_{2a}$ responses remained high. In this respect, it will be of interest in a future study to see whether the $IgG_1$: $IgG_{2a}$ response ratios as observed here reflect similar ratios for specific IFN-γ (Th1) and IL-4 (Th2 response) production in the spleens of immunised mice. As anticipated from the examples above, there were no significant differences between $IgG_1$ responses in the two experiments of FIG. 17 and FIGS. 19 and 20, where three and four injections of the plasmid were given, respectively, over 35 days.

It is generally accepted that efficient transfection with cationic liposomes relies on the cationic vesicle-DNA complexes (lipoplexes) possessing a slight excess of net positive charge that will allow binding of the complexes with the anionic cell surface. We have shown above that the positive surface charge of cationic liposomes is masked by plasma proteins that impose a net negative charge on the surface of the vesicles. It has been shown above in gel electrophoresis experiments that, whereas the plasmid in lipoplexes (obtained by mixing preformed cationic DRV or SUV with DNA) is easily displaced by sodium dodecyl sulphate (SDS) through anionic competition, this occurs only to a minor extent with liposome entrapped plasmid (generated as described in Section 2 by freeze-drying the lipoplexes and subsequent rehydration), presumably because, in the latter case, the plasmid is not as accessible to anions, especially to the much larger (than SDS) proteins. It is conceivable that the apparent failure in example 2 Table 5 more of complexes to mount a substantial immune response to the encoded antigen results from the displacement of complexed pRc/CMV HBS by proteins in the interstitial fluid.

It can therefore be surmised that, in contrast to the events associated with naked DNA immunisation by the intramuscular route, liposome-entrapped DNA given by the same route has a different fate. For instance, there is considerable degradation of naked DNA in situ, (Chatturgon et al) with some of the surviving material taken up by a minor fraction of myocytes (Davis, H L et al) and, probably (Chatturgon et al), a small number of APC thus requiring relatively large doses of the vaccine to provoke substantial responses. In contrast, liposome-entrapped DNA is largely protected (see example 9) from interstitial deoxyribonucleases by the bilayers surrounding the vaccine. Moreover, some of the liposomes (probably those of larger size) are expected to remain at the site of injection and slowly release their DNA content locally following their degradation by tissue phospholipases, with the surviving smaller vesicles delivering the remainder directly and efficiently to APC in the draining lymph nodes. Data obtained in an experiment where mice were injected intramuscularly with naked and liposome-entrapped pCMV.EGFP support this view. In these experiments fluorescence images of muscle and lymph node sections from mice injected intramuscularly were made with 10 μg liposome-entrapped or naked pCMV.EGFP and killed 48 h later. Sections from untreated animals were used as controls. Results indicate much greater fluorescence intensity (presumably reflecting greater expression of enhanced green fluorescent protein) in both the injected muscle and the draining popliteal and inguinal lymph nodes of mice treated with the liposomal plasmid than in the animals treated with the same amount of naked plasmid. At the intracellular level, it is likely that one of the steps in the pathway of liposome-mediated DNA immunisation, i.e. escape of DNA from endosomes following endocytosis of the DRV(DNA), is influenced by the composition of liposomes. Our results indicate that the fusogenic DOPE (or PE) and an appropriate surface charge (or zeta potential) contribute to optimal immune responses to the antigen encoded by the liposome-entrapped pRc/CMV HBS plasmid.

EXAMPLE 12

Induction of a Cytotoxic T Lymphocyte (CTL) Response to Plasmid DNA Delivered Via Liposomes Materials and Methods Materials Egg phosphatidylcholine (PC), dioleoyl phosphatidylethanolamine (DOPE) and 1,2-dioleoyl-3-(trimethylammonium)propane (DOTAP), ovalbumin (Grade VI) and cholera toxin were purchased from Sigma Chemical Co., UK. All lipids were stored (–20° C.) dissolved in chloroform and purged with nitrogen. Plasmid pCI-OVA (a kind gift of Dr. T. Nagata, Hamamatsu University School of Medicine, Japan) contains the chicken egg albumin protein (ovalbumin, OVA) CDNA cloned at the EcoR1 site of the pCI plasmid (Promega, Madison, Wis.) downstream from the CMV enhancer/promoter region. The plasmid for dosing was commercially produced by Aldevron (Fargo, USA) and contained <100 endotoxin units (EU)/mg of DNA with no residual protein detectable. Peptides for target cell (EL4) loaing was ovalbumin MHC class I restricted $(H-2^b)$[11] epitope (SIINFEKL) and a hepatitis B surface (HBS) antigen MHC class I restricted $(H-2^b)$ epitope (ILSPFLPL). They were prepared by F-MOC chemistry and purified (>90% purity) by reverse-phase HPLC. All other reagents were of appropriate analytical or tissue culture grade.

Methods

Preparation of liposome entrapped DNA Formulation.

Plasmid DNA pCI-OVA mixed with $^{35}$S-labelled (pCI-OVA) tracer, was entrapped in liposomes as described above. Briefly, small unilamellar vesicles (SUV) prepared from 16 μmoles egg phosphatidylcholine (PC), 8 μmoles dioleoyl phosphatidylcholine (DOPE) and 42 μmoles 1,2-dioleoyloxy-3-(trimethylammonium)propane (DOTAP) were mixed with 100 μg of plasmid DNA and freeze-dried overnight. Following rehydration under controlled conditions, [13, 14] the generated dehydrated-rehydrated vesicles (DRV liposomes) were centrifuged to remove non-incorporated DNA. The pellets were then resuspended in 0.1 M sodium phosphate buffer pH 7.2 supplemented with 0.9% NaCl (PBS) to the required dose volume. DNA incorporation into liposomes was estimated on the basis of $^{35}$S radioactivity recovered in the suspended pellets. Liposomes with entrapped DNA were subjected to microelectrophoresis.

Animal Procedures

Female C57BL/6 mice 6-12 weeks old (Harlan, UK) were immunised by subcutaneous injection. DNA doses of 10 µg and 2.5 µg (per mouse) as such (naked) or entrapped in liposomes (Lipodine™) were administered in 0.2 ml dose volume. Additional positive and negative controls received ovalbumin protein admixed with and cholera toxin, and PBS respectively. Mice received two doses of antigen at days 0 and 14, with sample bleeds collected from the tail vein at day 13. On day 21 all animals were terminally bled, culled by cervical dislocation and their spleens harvested, pooled and processed.

Enzyme Linked Immunosorbent Assay

Sera obtained from sample bleeds were diluted 20-fold in PBS and kept at −20° C. until assayed by the enzyme-linked immunoadsorbent assay (ELISA). Certified binding chemistry 96 well plates (Costar, EIA/RIA) were coated overnight at 4° C. with 100 µl/well of 60 µg/ml ovalbumin in 0.1 M sodium carbonate buffer (pH 9.6). After removing the excess ovalbumin solution, wells were coated with 200 µl of 2% (w/v) BSA in PBS. After 2 h at room temperature, the blocking solution was removed and doubling dilutions (starting with 1/100 dilution) of the different experimental sera samples were added to the wells (50 µl sample/well). Following 1 h incubation at 37° C. The wells were washed four times with PBS/Tween 20 and overlaid with 50 µl/well of rabbit anti-mouse total Ig HRP-conjugated sera (Dako). After 1 h at 37° C., plates were washed four times with PBS/Tween 20 and overlaid with 50 µl/well of substrate solution o-phenylenediamine (Sigma, Fast OPD). The reaction was stopped by adding 50 µl/well of stopping solution (3 M sulphuric acid) and the absorbance of each well at 490 nm was determined. The antibody response was expressed as the $\log_{10}$ of the reciprocal serum dilution required for OD to reach a reading of 0.200 (end point dilution). $\log_{10}$ values for sera from negative control animals was always lower than 2.0.

Cell Culture

The EL4 ($H-2^b$) cell line is a chemically induced mouse thymoma line derived from C57BL/6 mice (Gower et al). The cell line was maintained in RPMI-1640 (Sigma) supplemented with 50 IU/50 µg/ml of penicillin/streptomycin and 10% foetal calf serum (FCS) at 37° C. in a humidified atmosphere of 5% $CO_2$. Mouse splenocyte cultures were obtained from C57BL/6 mice and maintained in phenol red-free IMDM (Life Technologies) supplemented with 0.02 mM β-mercaptoethanol, 50 IU/50 µg/ml of penicillin/streptomycin, 0.01 mg/ml of apo-trasferrin, 1 mg/ml of bovine albumin, 0.015 mM linoleic acid and 0.015 mM oleic acid at 37° C. in a humidified atmosphere of 5% $CO_2$.

Mitomycin C Treatment of EL4 Cells

EL4 cultures in exponential phase were harvested by centrifugation (250 g, 5 min) and resuspended in serum-free RPMI-1640 medium containing 50 µg/ml of mitomycin C (Sigma). After 45 min incubation at 37° C., the cell suspension was washed four times in serum-free RPMI-1640 medium (250 g, 5 min) and finally resuspended in complete medium.

Preparation of Spenocyte Cell Cultures and CTL Assay

Mouse spleens were gently pressed between two frosted slides and red blood cells removed from the resulting cell suspension by treatment with Red Cell Lysis Buffer (9 parts 0.16M $NH_4Cl$ and 1 part of 0.17 M Tris, pH 7.2). Splenocyte suspensions from each experimental group were seeded in an upright 25 $cm^2$ flask at a density of $1.5 \times 10^6$ cells/ml containing, as stimulators for the CTL population, $10^5$ mitomycin C-treated EL4cells/ml, 10 µM of the OVA CTL epitope peptide and 10 U/ml of recombinant mouse interleukin-2 (IL-2). After 6 days incubation at 37° C., the splenocyte suspensions were harvested, resuspended in complete IMDM and tested for CTL activity, as effectors (E), against EL4 targets (T) using the CytoTox96™ LDH (lactate dehydrogenase) release colorimetric assay (Promega) according to a modification of the manufacturer's recommendations. This technology has been demonstrated to provide identical results (within the experimental error) to those determined in a parallel $^{51}Cr$ release assay (Korzenjewski et al and Decker et al). Briefly, EL4 targets were prepared from EL4 cultures harvested in exponential phase and resuspended at a density of $10^5$ cells/ml in either IMDM or IMDM containing 10 µM of a CTL epitope peptide (OVA or HBS). Assays were set up by seeding, in triplicate, three sets of doubling dilutions of effector splenocytes (from $2 \times 10^5$ cells/well to $5 \times 10^4$ cells/well) in U bottom 96-well plates (Nunc) in a volume of 50 µl/well. Each set of wells was then overlaid with 50 µl of either EL4 cells (effector spontaneous), EL4+OVA peptide (experimental) or EL4+ HBS peptide (experimental), resulting in E:T ratios of 40:1, 20:1 and 10:1. Duplicate sets of three wells containing only complete IMDM were also overlaid with 50 µl of one of the three EL4 target suspensions. These wells provide the minimum (target spontaneous) and, following complete cell lysis by a Triton X-100 solution, the maximum (target maximum) LDH release for each of the three EL4 target suspensions. After 4 h incubation at 37° C., 50 µl of supernatant was collected from each of the experimental and control wells and the LDH activity in the samples measured by colometric assay read at 490 nm. Cytotoxic activity at different E:T ratios was established from the optical density (OD) values at 490 nm and according to the following formula:

% Cytotoxicity

% Cytotoxicity =

$$\frac{OD_{experimental} - (OD_{effector\ spontaneous} + OD_{target\ spontaneous})}{OD_{target\ maximum} - OD_{target\ minimum}} \times 100$$

Results and Discussion

Liposome Characterisation

Incorporation values of DNA into the liposomes employing the DRV method were high (91±3%) (mean±SD, n=4) and consistent with values found in the above examples with pRc/CMV HBS plasmid DNA. Physical characterisation of the liposome formulations yielded a cationic zeta potential of 25±7 mV and a z-average diameter of 609±80 nm (mean±SD, n=4). Again, these values were not significantly different than those determined for liposomes containing pRc/CMV HBS plasmid DNA described above.

Immunology

Ideally, an effective vaccine must be stable without the need for cold storage and capable of inducing an effective immune response using only a small dose of antigen and without the need for multiple immunizations. DNA vaccines do, in principle, fulfil the first requirement described above, but most efficient vaccination procedures described up to date require either multiple deliveries of large doses of DNA or delivery of the DNA complexed with expensive gold particles. We have shown above that plasmid DNA entrapped in liposomes can induce an effective serum and mucosal antibody response. Nonetheless, the development of prophylactic and therapeutic immunity against viral infections and cancers requires the generation of a cytotoxic T cell (CTL) response in addition to the humoural response. To address the question of whether the use of these liposomes to deliver DNA vaccines results in the induction of both CTL and humoural responses, as well as in a reduction in the dose requirement, we have compared the immune response induced by two doses of DNA delivered either on their own or entrapped in liposomes by subcutaneous injection, a route not usually associated with the induction of immunity by DNA vaccines.

Vaccination with Liposomal DNA Induces an Increased Antibody Response

FIG. 21 shows the total serum antibody response to OVA+CT protein at days 13 (after first dose; upper frame) and 21 (after second dose; lower frame) in animals immunised with 2.5 µg (a, left hand frames) and 10 µg (b, right hand frames) of pCI-OVA either alone or entrapped in liposomes. LIPO DNA and DNA denote liposome entrapped DNA and naked DNA respectively.

As expected, all control animals immunised with 100 µg of OVA protein admixed with 1 µg of CT had seroconverted, developing a strong antibody response against OVA ($\log_{10}$>5) (not shown). This level of response is similar to that described elsewhere (Simmons et al) and contrasts with the lack of immunogenicity of the OVA protein when used in the absence of CT. In the test groups (FIG. 21a; upper frame) no antibody response against OVA could be detected in animals immunised with 2.5 µg of pCI-OVA after the first immunisation, independently of whether the DNA was delivered on its own or entrapped in liposomes. On the other hand, although no antibody response was detected in animals immunised with 10 µg of pCI-OVA alone (FIG. 21; upper frame), 50% (4/8) of animals immunised with 10 µg of pCI-OVA entrapped in lipsomes developed an OVA specific antibody response. This was lower than that induced in the control group (OVA protein admixed with CT) but was significantly different (t-test p<0.05) to that observed in the other experimental groups. After the second immunisation, there was a significant increase in the anti-OVA antibody response in the control animals ($\log_{10}$ titer>6) (not shown), as expected for a secondary response. In all experimental groups (FIGS. 21a and b, lower frame) significant differences were also observed. Over 60% (5/8) of the animals immunised with 2.5 µg of pCI-OVA entrapped in liposomes had now seroconverted, whilst only 12% (1/8) of the animals immunised with 2.5 µg of pCI-OVA alone had seroconverted. This difference was even more evident in animals immunised with 10 µg of pCI-OVA, since now only 25% of animals immunised with DNA alone had seroconverted whilst seroconversion was 100% (8/8) for the animals treated with DNA entrapped in liposomes.

These data clearly indicate that immunisation with DNA entrapped in liposomes significantly increases the antibody response to the plasmid encoded antigen, allowing for a reduction in the DNA dose necessary to induce a specific level of response. This last observation is evident by the fact that the level of the response and the degree of seroconversion observed for animals receiving 2 doses of 2.5 µg of pCI-OVA entrapped in liposomes is significantly higher than that observed in animals which received 2 doses of 10 µg of DNA alone.

Although these data show that seroconversion rates and antibody response levels are higher in the control (OVA+CT dosed) animals than in any of the experimental animals, this observation must be considered within the following context. Firstly, as indicated earlier, OVA protein alone has been reported to be a very poor immunogen, inducing little to no antibody responses. It is only when complexed to a very potent adjuvant like CT, which is certainly not licensed for human use, that the protein becomes highly immunogenic. Secondly, whilst in the control animals induction of the OVA specific immune response is immediate after injection, in the experimental groups there is a delay with regards to the time at which OVA protein first becomes available (following DNA expression) to the immune system. Finally, taking into account the reported levels of expression of plasmids in mammalian cells, the amount of protein produced even by the highest DNA dose used here (10 µg) will always be significantly lower than the amount of protein provided by any conventional immunisation protocol. These three factors together (lower immunogenicity of the non-complexed OVA protein produced by the plasmid, time delay in the availability of OVA protein to the immune system in animals immunised with DNA and the reduced levels of antigen available) are indeed those which define the differences in the level of the antibody response between control and experimental animals and can now be clearly understood.

Vaccination with Liposome Entrapped DNA Induces an Increased CTL Response

FIG. 22 shows CTL response to EL4 cells pulsed with an OVA CTL epitope peptide in animals immunised with 2.5 µg (a, left hand frame) and 10 µg (b, right hand frame) of pCI-OVA either alone or entrapped in liposomes ("Lipodine").

CTL responses are, as indicated earlier, essential for the resolution of viral infections and the treatment of established carcinomas. As shown in FIG. 22, control animals immunised with 100 µg of OVA protein complexed with 1 µg of CT generated a strong OVA specific CTL response (50% lysis at E:T 40:1). Animals immunised with 2.5 µg of pCI-OVA, independently of whether the DNA was delivered on its own or entrapped in liposomes generated no detectable CTL responses against OVA (FIG. 22a). Similarly, immunisation with 10 µg of pCI-OVA alone failed to induce any detectable CTL response (FIG. 22b). In contrast, animals immunised with 10 µg of pCI-OVA entrapped in liposomes generated an OVA specific CTL response (FIG. 22b) which was equal, if not higher, to that detected in the control animals.

Briefly, the induction of a CTL response depends on the effective presentation by professional antigen presenting cells of a large concentration of antigen-derived highly immunogenic CTL epitope peptides within an appropriate environment of cytokine and costimulatory molecules (Davies, D. H. et al). In our experiments, the CTL epitope peptides derived from the antigen used in the control and experimental immunisations are expected to be the same, independently of the method of delivery (protein, DNA or DNA entrapped in liposomes) and the presence of any adjuvant. In addition, the potential concentration of CTL epitope peptides derived from 100 µg of OVA protein would certainly be higher than that expected to be produced from a two 10 µg doses of pCI-OVA entrapped in liposomes. Considered together, these observations and our experimental results clearly indicate that delivery of DNA vaccines entrapped in liposomes result in more effective antigen presentation and immune activation, at least at the CTL level, that immunisation with DNA alone or protein complexed with a strong adjuvant.

In conclusion, entrapment of plasmid DNA vaccines in liposomes results in an increase in the antibody response to the plasmid encoded antigen compared to DNA alone, and in the induction of an antigen specific CTL response which is equal to, if not higher than, that achieved by immunisation with protein admixed with a strong adjuvant.

REFERENCES

Alton, E. W. F. W., Middleton, P. G., Caplen, N. J., Smith, S. N., Steel, D. M., Munkonge, F. M., Jeffery, P. K., Geddes, D. M., Hart, S. L., Williamson, R., Fasold, K. I., Miller, A. D., Dickinson, P., Stevenson, B. J., McLachlan, G., Dorin, J. R. and Porteous, D. J. (1993) Non-invasive liposome-mediated gene delivery can correct the ion transport defect in cystic fibrosis mutant mice Nat. Genet. 5, 135-142

Bangham, A. D., Hill, M. W. and Miller, N. G. A.(1974) Preparation and use of liposomes as models of biological membranes In: Korn, E. D. (ed.), Methods in Membrane Biology (New York, Plenum) pp. 1-68.

Bradford, M. M. (1976) A rapid and sensitive method for the quantitation of microgram quantities of protein utilizing the principle of protein-dye binding. Anal. Biochem. 72, 248-254.

Chattergon M A, Robinson T M, Boyer J D, Weiner D B. Specific immune induction following DNA-based immunization through in vivo transfection and activation of macrophages antigen presenting cells. J. Immunol 1998; 160: 5707-18.

Davies, D. H.; Stauss, H. J. The Significance of Human Leukocyte Antigen Associations with Cervical Cancer. Papillomavirus Report 1997, 8(2), 43-50.

Davis, D., Davies, A. and Gregoriadis, G. (1987) Immunology Letters, 14, 341-348.

Davis, H. L., Michel, M. L. and Whalen, R. G. (1993) "DNA-based immunisation . . . " Human Molecular Genetics 2, 1847-1851.

Davis, H. L., Demeneix, B. A., Quantin, B., Coulombe, J. and Whalen, R. G., Human Gene Therapy, 4, 733-740 (1993).

Davis, H. L., in Targeting of Drugs: Stategies for Oligonucleotide and Gene Delivery in Therapy, (eds Gregoriadis, G. and McCormack, B.) pp 21-29, (Plenum Press, NY, 1996).

Decker, T.; Lohmann-Matthes, M. L. A Quick and Simple Method for the Quantitation of Lactate Dehydrogenase Release in Measurements of Cellular Cytotoxicity and Tumor Necrosis Factor (TNF) Activity. J. Immunol. Meth. 1988, 115, 61.

Felgner, P. L. (1991) Gene Therapeutics, Nature 349, 351-352.

Gorer, P. A. Studies in Antibody Response of Mice to Tumor Inoculation. Br. J. Cancer 1950, 4. 372.

Gregoriadis, G. (1993) (ed.) Liposome Technology, 2nd Edition, Vols 1-3, CRC Press Inc., Boca Raton.

Gregoriadis, G (1995) Engineering Liposomes: Progress and Problems. Trends in Biotechnology (1995).

Gregoriadis, G., da Silva, H. and Florence, A. T. (1990) A procedure for the efficient entrapment of drugs in dehydration-rehydration liposomes (DRV). Int.J.Pharm. 65, 235-242.

Gregoriadis, G., Garcon, N., da Silva, H. and Sternberg, B. (1993) Coupling of ligands to liposomes independently of solute entrapment: Observations on the formed vesicles. Biochim. Biophys. Acta 1147, 185-193.

Gregoriadis, G., Saffie, R., and Hart S. L. (1996) J. Drug Targetting 3, 467-475.

Gregoriadis, G., Saffie, S. and De Souza, J. B. (1997) Liposome-mediated DNA vaccination. FEBS Lett. 402, 107-110.

Kay, M. A., Landen, C. N., Rothenberg, S. R., Taylor, 4 L. A., Leland, F., Wiehle, S., Fang, B., Bellinger, D., Finegold, M., Thompson, A. R., Read, M., Brinkhous, K. M. and Woo, S. L. C. (1994) In vivo hepatic gene therapy: Complete albeit transient correction of factor IX deficiency in haemophilia B dogs. Proc.Natl.Acad.Sci.USA 91, 2353-2357.

Kirby, C. and Gregoriadis, G. (1984) Dehydration-rehydration vesicles (DRV): A new method for high yield drug entrapment in liposomes. Biotechnology 2, 979-984.

Korzeniewski, C.; Callewaert, D. M. An Enzyme-Release Assay for Natural Cytotoxicity. J. Immunol. Meth. 1983, 64, 313.

Legendre, Y.-Y. and Szoka Jr., F. C. (1995) Liposomes for gene therapy, In: Liposomes, New Systems and New Trends in their Applications (Puissieux, F., Couvreur, P., Delattre, J. and Devissaugnet, J. P. eds.) (Paris, Editions de Sante), pp. 669-692.

Mulligan, R. C. (1993) The basic science of gene therapy. Science 260, 926-932.

Nakane, A., Numata, A. and Minagawa, T., Infect. Immun., 60, 523-528 (1992).

Raz, E., Carson, D., Rhodes, H. G., Abal, M. A., Tsai, J. Y., Wheeler, J. C., Morrow, J., Felgner, P. L. and Baird, M. S. (1994) In: Vaccines, Cold Spring Harbour Laboratory Press, Cold Spring Harbor.

Raz, E. et al, Proc.Natl.Acad.Sci.USA,91,9519-9523 (1994).

Scherphof, G., van Leeuwen, B., Wilschut, J. C. and Damen, J. (1983) Exchange of phosphatidylcholine between small unilamellar liposomes and human plasma high-density lipo-protein involves exclusively the phospholipid in the outer monolayer of the liposomal membrane. Biochim.Biophys.Acta 732, 595-599.

Simmons, C. P.; Mastroeni, P.; Fowler, R.; Ghaemmaghami, M.; Lycke, N.; Pizza, M.; Rappuoli, R.; Dougan, G. MHC Class I-Restricted Cytotoxid Lymphocyte Responses Induced by Enterotoxin-Based Mucosal Adjuvants. J. Immunol. 1999, 163(12), 6502-6510.

de Souza, J. B., Ling, I. T., Ogun, S. A., Holder, A. A. and Playfair, J. H. L. Infect.Immun., 64, 3532-3536 (1996).

Tan, L. and Gregoriadis, G. (1989) The effect of positive surface charge of liposomes on their clearance from blood and its relation to vesicle lipid composition. Biochem.Soc-.Trans. 17, 690-691.

Wheeler, V. C. and Coutelle, C. (1995) Non-degradative in vitro labelling of plasmid DNA. Anal. Biochem. 225, 374-376.

Zhu, N., Liggit, D., Liu, Y. and Debs, R. (1993) Systemic gene expression after intravenous DNA delivery into adult mice. Science, 261, 209-211.

The invention claimed is:

1. A method to generate both a cell-based and humoral immune response to a target polypeptide in an animal, which method comprises administering subcutaneously or intramuscularly to the animal a composition comprising liposomes suspended in an aqueous liquid and a polynucleotide comprising a promoter operatively linked to a nucleotide sequence encoding said target polypeptide, wherein the liposomes comprise phosphatidylcholine (PC), dioleoyl phosphatidyl ethanolamine (DOPE), and 1,2-dioleoyloxy-3-trimethyl ammonium propane (DOTAP), have diameters in the range 100 to 2000 nm and comprise a lipid bilayer and an aqueous intravesicular space, wherein said polynucleotide is entrapped in the aqueous intravesicular space, wherein said lipid bilayer includes said DOTAP in an amount such that the lipid bilayer has an overall cationic charge;

whereby said polynucleotide is delivered to and is expressed in target cells whereby an immune response including an IgG response and Th1 and Th2 responses to the target polypeptide result;

wherein said polynucleotide is administered in an amount sufficient to elicit said immune response.

2. The method of claim 1, wherein said composition has been prepared by a process that comprises mixing an aqueous suspension of empty liposomes with said polynucleotide to form a mixed suspension, dehydrating the mixed suspension to form a dehydrated mixture, and rehydrating the dehydrated mixture in an aqueous liquid to form liposomes which are dehydration-rehydration vesicles (DRVs) containing the polynucleotide in the intravesicular space.

3. The method of claim 2, wherein said process further includes subjecting said polynucleotide-containing DRVs to microfluidization or extrusion.

4. The method of claim 1, wherein the composition is administered intramuscularly.

5. A process for forming an aqueous suspension of liposomes having diameters in the range 100 to 2000 nm comprising the steps:

a) providing an aqueous suspension of small unilamellar vesicles formed from the liposome-forming agents phosphatidylcholine (PC), dioleoyl phosphatidyl ethanolamine (DOPE), and 1,2-dioleoyloxy-3-trimethyl ammonium propane (DOTAP), wherein said DOTAP is present in an amount whereby the small unilamellar vesicles have an overall cationic charge;

b) adding to the aqueous suspension of small unilamellar vesicles a nucleic acid including a promoter operatively linked to a nucleotide sequence encoding an immunogenic polypeptide to form a mixed suspension in which the weight ratio of liposome forming components making up the small unilamellar vesicles in step (a) to the nucleic acid added in step (b) is in the range (50 to 10000):1;

c) dehydrating the mixed suspension to form a dehydrated mixture;

d) rehydrating the dehydrated mixture to form an aqueous suspension of liposomes that are dehydration-rehydration vesicles (DRVs) containing said nucleic acid in an intravesicular space thereof; and e) optionally subjecting the aqueous suspension of DRVs to microfluidisation whereby said aqueous suspension of liposomes is produced.

6. The process of claim 5 further comprising removing non-entrapped nucleic acid from the aqueous suspension of DRVs.

7. A composition for administration to an animal to induce a cell-based and humoral immune response to a polypeptide, which composition comprises liposomes having diameters in the range 100 to 2000 nm and having lipid-bilayers surrounding aqueous intravesicular spaces and a polynucleotide comprising a promoter operatively linked to a nucleotide sequence encoding said target polypeptide, which lipid-bilayers are formed from liposome forming components that comprise phosphatidylcholine (PC), dioleoyl phosphatidyl ethanolamine (DOPE), and 1,2-dioleoyloxy-3-trimethyl ammonium propane (DOTAP), and wherein said DOTAP is in an amount to confer an overall cationic charge on the liposomes, and wherein the polynucleotide is entrapped in the aqueous intravesicular space.

8. The composition of claim 7, wherein the liposomes are suspended in a pharmaceutically acceptable aqueous vehicle.

9. The composition of claim 7, wherein the polypeptide is a viral polypeptide.

10. The composition of claim 9, wherein the viral polypeptide is a polypeptide of hepatitis B, hepatitis C, influenza or human immunodeficiency virus.

11. The composition of claim 10, wherein the viral polypeptide is hepatitis B surface antigen or haemagglutinin.

* * * * *